United States Patent
Del Giudice et al.

(10) Patent No.: US 9,901,630 B2
(45) Date of Patent: *Feb. 27, 2018

(54) ADJUVANT-SPARING MULTI-DOSE INFLUENZA VACCINATION REGIMEN

(71) Applicant: Seqirus UK Limited, Berkshire (GB)

(72) Inventors: Giuseppe Del Giudice, Siena (IT); Riccardo Manetti, Siena (IT)

(73) Assignee: Seqirus UK Limited, Maidenhead, Berkshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/326,299

(22) Filed: Jul. 8, 2014

(65) Prior Publication Data

US 2014/0370053 A1    Dec. 18, 2014

Related U.S. Application Data

(63) Continuation of application No. 13/236,538, filed on Sep. 19, 2011, now Pat. No. 8,808,686, which is a continuation of application No. 12/304,919, filed as application No. PCT/IB2007/002724 on Jun. 15, 2007, now abandoned.

(60) Provisional application No. 60/814,665, filed on Jun. 15, 2006.

(51) Int. Cl.
*A61K 39/145* (2006.01)
*C12N 7/00* (2006.01)
*A61K 39/12* (2006.01)
*A61K 39/00* (2006.01)

(52) U.S. Cl.
CPC ............ *A61K 39/145* (2013.01); *A61K 39/12* (2013.01); *C12N 7/00* (2013.01); *A61K 2039/5252* (2013.01); *A61K 2039/545* (2013.01); *A61K 2039/55566* (2013.01); *C12N 2760/16034* (2013.01); *C12N 2760/16134* (2013.01)

(58) Field of Classification Search
CPC .......... A61K 2039/55511; A61K 2039/55566; A61K 39/145; A61K 2039/5252; A61K 2039/55561; C12N 2760/16034; C12N 2760/16111; C12N 2760/16234; C12N 7/00; C07K 16/1018; G01N 2333/11; A61M 2202/30

See application file for complete search history.

(56) References Cited

U.S. PATENT DOCUMENTS

| | | | |
|---|---|---|---|
| 7,238,349 | B1 | 7/2007 | D'Hondt et al. |
| 2004/0047882 | A1 | 3/2004 | Broeker |
| 2007/0141078 | A1 | 6/2007 | D'Hondt et al. |
| 2008/0181911 | A1* | 7/2008 | Hanon ................. A61K 39/145 424/206.1 |

FOREIGN PATENT DOCUMENTS

| | | |
|---|---|---|
| WO | WO-90/01948 A1 | 3/1990 |
| WO | WO-01/22992 | 4/2001 |
| WO | WO-2005/002621 A2 | 1/2005 |
| WO | WO-2005/107797 | 11/2005 |
| WO | WO-2006/100109 A1 | 9/2006 |
| WO | WO-2006/100110 A1 | 9/2006 |
| WO | WO-2007/052057 | 5/2007 |
| WO | WO-2007/068907 A2 | 6/2007 |
| WO | WO-2008/009309 A1 | 1/2008 |

OTHER PUBLICATIONS

Nicholson et al. Lancet 2001, vol. 357, pp. 1937-1943.*
Ott et al. Chapter 10, MF59, Design and Evaluation of a safe and potent Adjuvant for human vaccines from p. 277-296 in Vaccine Design: The Subunit and Adjuvant Approach, edited by Michael F. Powell and Mark J. Newman. Plenum Press, New York, 1995.*
Ruden FL Clin. Infect Diseases, Mar. 1, 2004, 38 (5), pp. 678-688.*
Abbas et al. (1994). "Cellular and molecular immunology," W.B. Saunders Company, 2nd Edition, p. 7-12.
Aventis Pasteur (2002). "Influenza Virus Vaccine Fluzone©: 2002-2003 formula," product description, 8 pages.
Banzhoff et al. (2003). "A new MF59-adjuvanted influenza vaccine enhances the immune response in the elderly with chronic diseases: results from an immunogenicity meta-analysis," Gerontology 49:177-184.
Castiglione et al. (2012). "How the interval between prime and boost injection affects the immune response in a computational model of the immune system," Computational and mathematical methods in medicine 2012(Article ID 842329):9 pages.
CDC—Center for Disease Prevention and Control (accessed in 2013). "CDC statement on narcolepsy following Pandemrix influenza vaccination in Europe," available online at <http://www.cdc.gov/vaccinesafety/Concerns/h1n1_narcolepsy_pandemrix.html>.
Del Giudice et al. (Oct. 15, 2001). "What are the limits of adjuvanticity?" Vaccine 20(suppl 1):S38-S41.
Dillon et al. (1992). "Induction of protective class I MHC-restricted CTL in mice by a recombinant influenza vaccine in aluminium hydroxide adjuvant," Vaccine 10(5):309-318.
Doshi (2011). "The elusive definition of pandemic influenza," Bull World Health Organ 89:532-538.
Frey et al. (2003). "Comparison of the safety, tolerability, and immunogenicity of a MF59-adjuvanted influenza vaccine and a non-adjuvanted influenza vaccine in non-elderly adults," Vaccine 21:4234-4237.
Granoff et al. (May 1997). "MF59 Adjuvant Enhances Antibody Responses of Infant Baboons Immunized with Haemophilus influenza Type b and Neisseria meningitidis Group C Oligosaccharide-CRM197 Conjugate Vaccine" Infect Immun 65(5):1710-1715.

(Continued)

*Primary Examiner* — Bao Li
(74) *Attorney, Agent, or Firm* — Finnegan, Henderson, Farabow, Garrett & Dunner, LLP

(57) ABSTRACT

An influenza vaccine is administered by a multi-dose regimen, in which (i) a first dose is administered with an adjuvant and (ii) a later dose is administered either without an adjuvant or with a different adjuvant. Thus the invention provides the benefits of a two-dose regimen without also doubling the supply need for a given adjuvant.

22 Claims, 1 Drawing Sheet

(56) References Cited

OTHER PUBLICATIONS

Guy et al. (Sep. 1998). "Effects of the Nature of Adjuvant and Site of Parenteral Immunization on the Serum and Mucosal Immune Responses Induced by a Nasal Boost with a Vaccine Alone" Clinical and Diagnostic Laboratory Immunology 5(5):732-736.
Harper et al. (2005). "Weekly report: Prevention and control of RR-8 influenza. Recommendation of the Advisory Committee of Immunization Practices (ACIP)," Morbidity and Mortality 54(RR-8), 44 pages.
Lopez et al. (2011). "Combined, concurrent and sequential administration of seasonal influenza and MF-59-adjuvanted A/H5N1 vaccines: A phase II randomized, controlled trial of immunogenicity and safety in healthy adults," J Infect Dis 203:1719-1728.
Minutello et al. (1999). "Safety and immunogenicity of an inactivated subunit influenza virus vaccine combined with MF59 adjuvant emulsion in elderly subjects, immunized for three consecutive influenza seasons," Vaccine 17:99-104.
Monto (2006). "Vaccines and antiviral drugs in pandemic preparedness," Emerg Infect Dis 12(1):55-60.
Nicholson et al. (2001). "Safety and antigenicity of non-adjuvanted and MF59-adjuvant influenza A/Duck/Singapore/97 (H5N3) vaccine: a randomized trial of two potential vaccines against H5N1 influenza," Lancet 357:1937-1943.
Novartis Vaccines (2007). "2005-2007 Research Report," pp. 168-169.
O'Hagan (2000). "Vaccine adjuvants: Preparation methods and research protocols," Humana Press.
Podda (2001). "The adjuvanted influenza vaccines with novel adjuvants: experience with the MF59-adjuvanted vaccine," Vaccine 19:2673-2680.
Song et al. (2013). "Long-term and cross reactive immunogenicity of inactivated trivalent influenza vaccine in the elderly: MF59-adjuvanted vaccine versus unadjuvanted vaccine," J Med Virol 85:1591-1597.
Stephenson et al. (2005). "Cross-reactivity to highly pathogenic avian influenza H5N1 viruses after vaccination with nonadjuvanted and MF59-adjuvanted influenza A/Duck/Singapore/97 (H5N3) vaccine: a potential primary strategy," J Infect Dis 191:1210-1215.
Treanor et al. (2006). "Safety and immunogenicity of an inactivated subvirion influenza (H5N1) vaccine," NEJM 354(13):1343-1351.
U.S. Department of health and Human Services NIH News releases on Sep. 25, 2006, pp. 1-2.
Wadman (2005). "Race is on for the flu vaccine," Nature 438:23.
Wong et al. (2005). "Influenza vaccination: options and issues," Hong Kong Medical Journal 11(5):381-390.
World Health Organization (accessed in 2013). "Squalene-based adjuvants in vaccines," available online at <http://www.who.int/vaccine_safety/committee/topics/adjuvants/squalene/questions_and_answers/en/>.
Assignment data from USPTO for U.S. Appl. No. 12/304,919 recorded Mar. 26, 2009. 1 page.
CDC—Center for Disease Prevention and Control. (2005). "Prevention and Control of Influenza," Morbidity and Mortality Weekly Report (MMWR), vol. 54, No. RR-8. 44 pages.
CDC—Center for Disease Prevention and Control. (accessed 2015) "Self-reported influenza vaccination coverage trends 1989-2008 among adults by age group, risk group, race/ethnicity, health-care worker status, and pregnancy status, United States, National Health Interview Survey (NHIS)" 2 pages. <http://www.cdc.gov/flu/pdf/professionals/nhis89_08fluvaxtrendtab.pdf>.
Chiron Behring, (2003). "Product Information: FLUAD 2003-2004" in German, cited as D9 in the Statement of Grounds of Opposition by Sanofi Pasteur Inc. For EP2032163 dated Oct. 23, 2013. 2 pages.
Declaration for Professor Charalambos P. Kyriacou dated Sep. 15, 2014, filed in the opposition proceedings for EP2032163. 3 pages.
Declaration of Dr. Atsuko Polzin, Esq. dated Apr. 6, 2016, filed in the opposition proceedings for EP2032163. 2 pages.
Declaration of Gabriel Cuonzo dated Apr. 6, 2016, filed in the opposition proceedings for EP2032163. 3 pages.
Italian Health Minister Annual Communication, (May 31, 2001) "Prevention and control of the influenza: recommendations for the 2001-2002 season" 15 pages (with English translation).
Notice of Opposition by Glaxosmithkline Biologicals SA for EP2032163, dated Oct. 23, 2013. 22 pages.
Notice of Opposition by Sanofi Pasteur Inc. for EP2032163, dated Oct. 23, 2013. 55 pages.
Patentee's Reply to the Notice of Opposition for EP2032163, dated Apr. 7, 2016. 8 pages.
US FDA, News Release (Nov. 22, 2013) "FDA approves first adjuvanted vaccine for prevention of H5N1 avian influenza," accessed Aug. 28, 2014. 1 page. <http://www.fda.gov/newsevents/newsroom/pressannouncements/ucm376444.htm>.
US FDA, Vaccines, Blood & Biologicals, (updated on May 1, 2014) "Influenza A (H5N1) Virus Monovalent Vaccine, Adjuvanted, manufactured by ID Biomedical Corporation—Questions and Answers" accessed Aug. 28, 2014. 4 pages. <http://www.fda.gov/BiologicsBloodVaccines/SafetyAvailability/VaccineSafety/ucm376465.htm>.
U.S. Appl. No. 60/814,665, filed Jun. 15, 2006. 40 pages.

* cited by examiner

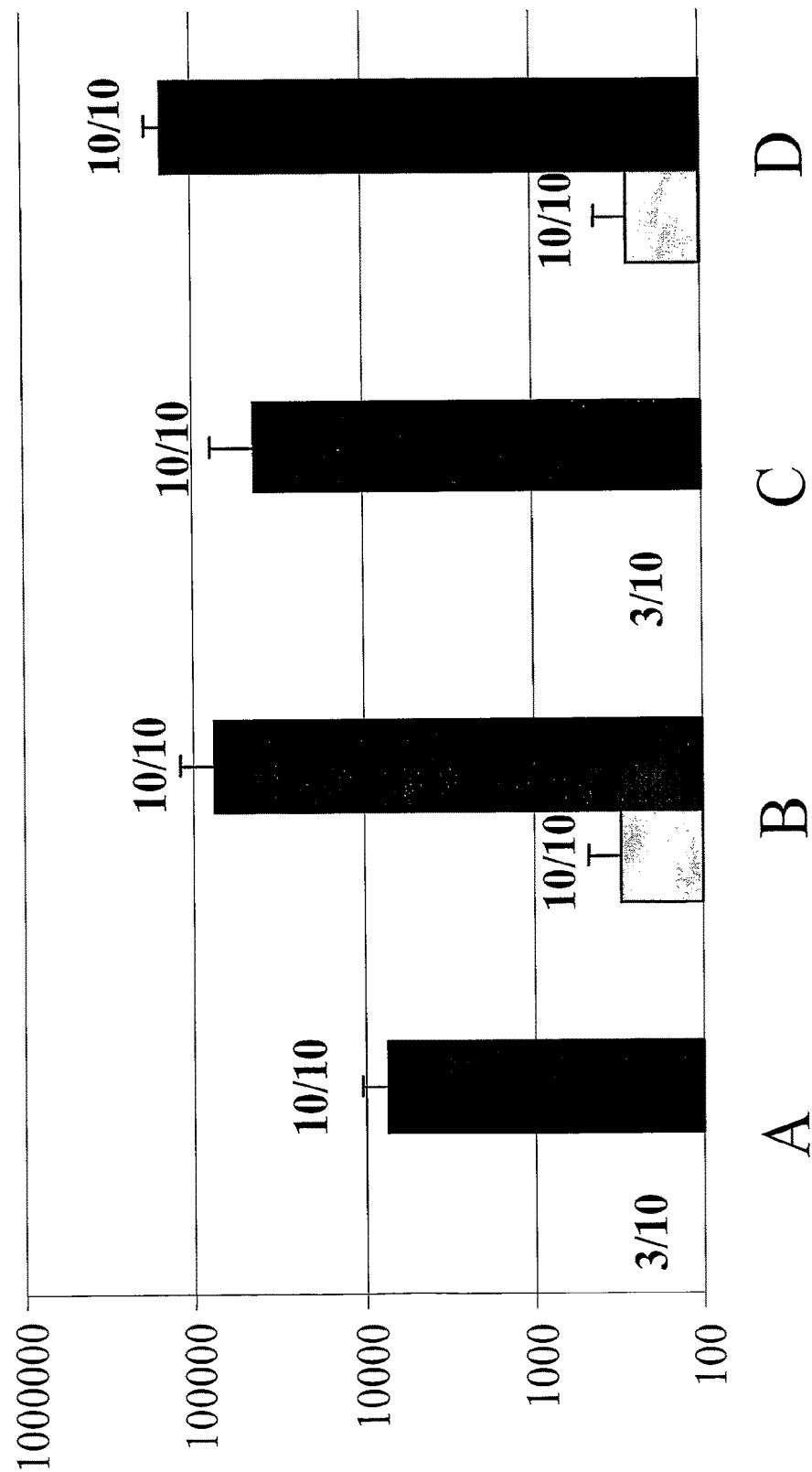

ADJUVANT-SPARING MULTI-DOSE INFLUENZA VACCINATION REGIMEN

CROSS REFERENCE TO RELATED APPLICATIONS

This application is a Continuation of U.S. patent application Ser. No. 13/236,538, filed Sep. 19, 2011; which is a Continuation of U.S. patent application Ser. No. 12/304,919, with an international filing date of Jun. 15, 2007, now Abandoned; which is a National Phase of International Patent Application No. PCT/IB2007/002724, filed Jun. 15, 2007; which claims the benefit of U.S. Provisional Patent Application No. 60/814,665, filed Jun. 15, 2006, all of which are incorporated herein by reference in their entirety.

TECHNICAL FIELD

This invention is in the field of vaccines for protecting against influenza virus infection.

BACKGROUND ART

Patients receiving influenza vaccines are currently given one dose every year, except that the first time that the vaccine is given to a child aged 8 years or below they receive two doses separated by at least four weeks.

It is thought (e.g. see ref. 1) that a two-dose regimen will also be required in a pandemic situation, where the human population is immunologically naïve to a new influenza virus strain.

The need for two doses means that, with a fixed supply of antigen, the number of doses that can be made is half of the number that could be made with a one-dose regimen. Thus it has been proposed to use a lower amount of antigen per dose, and to use an adjuvant to compensate for this reduction.

If a one-dose regimen of an adjuvanted vaccine does not elicit a sufficient immune response, however, then a two-dose regimen will be required anyway, with the additional disadvantage that the supply of adequate amounts of adjuvant will also then be an issue. In a situation where hundreds of millions of adjuvanted vaccine doses are being prepared then this issue will be very important, and will be particularly important for synthetic adjuvants.

It is an object of the invention to reduce or avoid this disadvantage.

DISCLOSURE OF THE INVENTION

According to the invention, an influenza vaccine is administered by a multi-dose regimen, in which (i) a first dose is administered with an adjuvant and (ii) a later dose is administered either without an adjuvant or with a different adjuvant. Thus the invention provides the benefits of a two-dose regimen without also doubling the supply need for a given adjuvant. The first dose and the later dose should preferably given by the same administration route (e.g. both by intramuscular injection), whereas the study in reference 2 used an unadjuvanted mucosal booster as a third dose in a three-dose regimen in order to determine whether the parenteral priming route in mice (back vs. neck) affected the immunogenicity of an adjuvanted vaccine.

Thus the invention provides a method for immunizing a patient against influenza virus infection, comprising the steps of: (i) administering a dose of influenza virus vaccine in combination with a first adjuvant; and (ii) administering a further dose of influenza virus vaccine without that adjuvant. The further dose may include no adjuvant or may include a second adjuvant that is different from the first adjuvant.

The invention also provides a kit comprising: (i) a first influenza virus vaccine in combination with a first adjuvant; and (ii) a second influenza virus vaccine without that adjuvant. The invention also provides the use of (i) a first influenza virus vaccine in combination with a first adjuvant; and (ii) a second influenza virus vaccine without that adjuvant, in the manufacture of a multi-dose influenza vaccine. The second vaccine may include no adjuvant or may include a second adjuvant that is different from the first adjuvant.

The invention also provides a method for completing the immunization of a patient against influenza virus infection, wherein the patient has previously received a dose of influenza virus vaccine in combination with a first adjuvant, and wherein the method comprises the step of administering to that patient a further dose of influenza virus vaccine without that adjuvant. The further dose may include no adjuvant or may include a second adjuvant that is different from the first adjuvant.

The invention also provides the use of an unadjuvanted influenza virus vaccine in the manufacture of a medicament for immunizing a patient against influenza virus infection, wherein that patient has previously received an adjuvanted influenza virus vaccine. The invention also provides the use of a second adjuvanted influenza virus vaccine in the manufacture of a medicament for immunizing a patient against influenza virus infection, wherein that patient has previously received a first adjuvanted influenza virus vaccine, wherein the adjuvants in the first and second influenza virus are not the same.

These methods, kits and uses are particularly advantageous if the hemagglutinin doses in the two vaccinations are lower than the standard 15 µg per strain per dose, as the invention then permits relaxation of requirements for both antigen and adjuvant.

The Influenza Virus Antigen

Vaccines used with the invention include an influenza virus antigen. The antigen will typically be prepared from influenza virions but, as an alternative, antigens such as haemagglutinin and neuraminidase can be expressed in a recombinant host (e.g. in an insect cell line using a baculovirus vector) and used in purified form [3,4,5]. In general, however, antigens will be from virions.

The antigen may take the form of a live virus or, more preferably, an inactivated virus. Chemical means for inactivating a virus include treatment with an effective amount of one or more of the following agents: detergents, formaldehyde, formalin, β-propiolactone, or UV light. Additional chemical means for inactivation include treatment with methylene blue, psoralen, carboxyfullerene (C60) or a combination of any thereof. Other methods of viral inactivation are known in the art, such as for example binary ethylamine, acetyl ethyleneimine, or gamma irradiation. The INFL-EXAL™ product is a whole virion inactivated vaccine.

Where an inactivated virus is used, the vaccine may comprise whole virion, split virion, or purified surface antigens (including hemagglutinin and, usually, also including neuraminidase).

Typically, each vaccine dose in a multi-dose regimen will use the same form of antigen e.g. it will not use a split virion vaccine for a first dose and a whole virion vaccine for a second dose.

Virions can be harvested from virus-containing fluids by various methods. For example, a purification process may involve zonal centrifugation using a linear sucrose gradient solution that includes detergent to disrupt the virions. Antigens may then be purified, after optional dilution, by diafiltration.

Split virions are obtained by treating virions with detergents (e.g. ethyl ether, polysorbate 80, deoxycholate, tri-N-butyl phosphate, Triton X-100, Triton N101, cetyltrimethylammonium bromide, Tergitol NP9, etc.) to produce subvirion preparations, including the 'Tween-ether' splitting process. Methods of splitting influenza viruses are well known in the art e.g. see refs. 6-11, etc. Splitting of the virus is typically carried out by disrupting or fragmenting whole virus, whether infectious or non-infectious with a disrupting concentration of a splitting agent. The disruption results in a full or partial solubilisation of the virus proteins, altering the integrity of the virus. Preferred splitting agents are non-ionic and ionic (e.g. cationic) surfactants e.g. alkylglycosides, alkylthioglycosides, acyl sugars, sulphobetaines, betains, polyoxyethylenealkylethers, N,N-dialkyl-Glucamides, Hecameg, alkylphenoxy-polyethoxyethanols, quaternary ammonium compounds, sarcosyl, CTABs (cetyl trimethyl ammonium bromides), tri-N-butyl phosphate, Cetavlon, myristyltrimethylammonium salts, lipofectin, lipofectamine, and DOT-MA, the octyl- or nonylphenoxy polyoxyethanols (e.g. the Triton surfactants, such as Triton X-100 or Triton N101), polyoxyethylene sorbitan esters (the Tween surfactants), polyoxyethylene ethers, polyoxyethlene esters, etc. One useful splitting procedure uses the consecutive effects of sodium deoxycholate and formaldehyde, and splitting can take place during initial virion purification (e.g. in a sucrose density gradient solution). Thus a splitting process can involve clarification of the virion-containing material (to remove non-virion material), concentration of the harvested virions (e.g. using an adsorption method, such as CaHPO$_4$ adsorption), separation of whole virions from non-virion material, splitting of virions using a splitting agent in a density gradient centrifugation step (e.g. using a sucrose gradient that contains a splitting agent such as sodium deoxycholate), and then filtration (e.g. ultrafiltration) to remove undesired materials. Split virions can usefully be resuspended in sodium phosphate-buffered isotonic sodium chloride solution. The BEGRIVAC™, FLUARIX™, FLUZONE™ and FLUSHIELD™ products are split vaccines.

Purified surface antigen vaccines comprise the influenza surface antigens haemagglutinin and, typically, also neuraminidase. Processes for preparing these proteins in purified form are well known in the art. The FLUVIRIN™, AGRIPPAL™ and INFLUVAC™ products are subunit vaccines.

Influenza antigens can also be presented in the form of virosomes [12] (nucleic acid free viral-like liposomal particles), as in the INFLEXAL V™ and INVAVAC™ products, but it is preferred not to use virosomes with the present invention. Thus, in some embodiments, the influenza antigen is not in the form of a virosome.

The influenza virus may be attenuated. The influenza virus may be temperature-sensitive. The influenza virus may be cold-adapted. These three features are particularly useful when using live virus as an antigen.

Influenza virus strains for use in vaccines change from season to season. In the current inter-pandemic period, vaccines typically include two influenza A strains (H1N1 and H3N2) and one influenza B strain, and trivalent vaccines are typical. The invention can be use with these vaccines, but is particularly useful for viruses from pandemic strains (i.e. strains to which the vaccine recipient and the general human population are immunologically naïve), such as H2, H5, H7 or H9 subtype strains (in particular of influenza A virus), and influenza vaccines for pandemic strains may be monovalent or may be based on a normal trivalent vaccine supplemented by a pandemic strain. Depending on the season and on the nature of the antigen included in the vaccine, however, the invention may protect against one or more of influenza A virus hemagglutinin subtypes H1, H2, H3, H4, H5, H6, H7, H8, H9, H10, H11, H12, H13, H14, H15 or H16. The invention may protect against one or more of influenza A virus NA subtypes N1, N2, N3, N4, N5, N6, N7, N8 or N9.

Other strains that can usefully be included in the compositions are strains which are resistant to antiviral therapy (e.g. resistant to oseltamivir [13] and/or zanamivir), including resistant pandemic strains [14].

The invention is particularly useful for immunizing against pandemic strains. The characteristics of an influenza strain that give it the potential to cause a pandemic outbreak are: (a) it contains a new hemagglutinin compared to the hemagglutinins in currently-circulating human strains, i.e. one that has not been evident in the human population for over a decade (e.g. H2), or has not previously been seen at all in the human population (e.g. H5, H6 or H9, that have generally been found only in bird populations), such that the human population will be immunologically naive to the strain's hemagglutinin; (b) it is capable of being transmitted horizontally in the human population; and (c) it is pathogenic to humans. A virus with H5 haemagglutinin type is preferred for immunising against pandemic influenza, such as a H5N1 strain. Other possible strains include H5N3, H9N2, H2N2, H7N1 and H7N7, and any other emerging potentially pandemic strains. Within the H5 subtype, a virus may fall into HA clade 1, HA clade 1', HA clade 2 or HA clade 3 [15], with clades 1 and 3 being particularly relevant.

Typically, each vaccine dose in a multi-dose regimen will share at least one common hemagglutinin subtype e.g. the invention will not use a monovalent H5N1 vaccine for a first dose but a monovalent H9N2 vaccine for a second dose.

Compositions of the invention may include antigen(s) from one or more (e.g. 1, 2, 3, 4 or more) influenza virus strains, including influenza A virus and/or influenza B virus. Where a vaccine includes more than one strain of influenza, the different strains are typically grown separately and are mixed after the viruses have been harvested and antigens have been prepared. Thus a process of the invention may include the step of mixing antigens from more than one influenza strain. For pandemic situations, however, a monovalent vaccine may be preferred.

The influenza virus may be a reassortant strain, and may have been obtained by reverse genetics techniques. Reverse genetics techniques [e.g. 16-20] allow influenza viruses with desired genome segments to be prepared in vitro using plasmids. Typically, it involves expressing (a) DNA molecules that encode desired viral RNA molecules e.g. from polI promoters, and (b) DNA molecules that encode viral proteins e.g. from polII promoters, such that expression of both types of DNA in a cell leads to assembly of a complete intact infectious virion. The DNA preferably provides all of the viral RNA and proteins, but it is also possible to use a helper virus to provide some of the RNA and proteins. Plasmid-based methods using separate plasmids for producing each viral RNA are preferred [21-23], and these methods will also involve the use of plasmids to express all or some (e.g. just the PB1, PB2, PA and NP proteins) of the viral proteins, with up to 12 plasmids being used in some methods.

To reduce the number of plasmids needed, a recent approach [24] combines a plurality of RNA polymerase I transcription cassettes (for viral RNA synthesis) on the same plasmid (e.g. sequences encoding 1, 2, 3, 4, 5, 6, 7 or all 8 influenza A vRNA segments), and a plurality of protein-coding regions with RNA polymerase II promoters on another plasmid (e.g. sequences encoding 1, 2, 3, 4, 5, 6, 7 or all 8 influenza A mRNA transcripts). Preferred aspects of the reference 24 method involve: (a) PB1, PB2 and PA mRNA-encoding regions on a single plasmid; and (b) all 8 vRNA-encoding segments on a single plasmid. Including the NA and HA segments on one plasmid and the six other segments on another plasmid can also facilitate matters.

As an alternative to using polI promoters to encode the viral RNA segments, it is possible to use bacteriophage polymerase promoters [25]. For instance, promoters for the SP6, T3 or T7 polymerases can conveniently be used. Because of the species-specificity of polI promoters, bacteriophage polymerase promoters can be more convenient for many cell types (e.g. MDCK), although a cell must also be transfected with a plasmid encoding the exogenous polymerase enzyme.

In other techniques it is possible to use dual polI and polII promoters to simultaneously code for the viral RNAs and for expressible mRNAs from a single template [26,27].

Thus the virus, particularly an influenza A virus, may include one or more RNA segments from a A/PR/8/34 virus (typically 6 segments from A/PR/8/34, with the HA and N segments being from a vaccine strain, i.e. a 6:2 reassortant), particularly when viruses are grown in eggs. It may also include one or more RNA segments from a A/WSN/33 virus, or from any other virus strain useful for generating reassortant viruses for vaccine preparation. Typically, the invention protects against a strain that is capable of human-to-human transmission, and so the strain's genome will usually include at least one RNA segment that originated in a mammalian (e.g. in a human) influenza virus. It may include NS segment that originated in an avian influenza virus.

The viruses used as the source of the antigens can be grown either on eggs or on cell culture. The current standard method for influenza virus growth uses specific pathogen-free (SPF) embryonated hen eggs, with virus being purified from the egg contents (allantoic fluid). More recently, however, viruses have been grown in animal cell culture and, for reasons of speed and patient allergies, this growth method is preferred. If egg-based viral growth is used then one or more amino acids may be introduced into the allantoid fluid of the egg together with the virus [11].

When cell culture is used, the viral growth substrate will typically be a cell line of mammalian origin. Suitable mammalian cells of origin include, but are not limited to, hamster, cattle, primate (including humans and monkeys) and dog cells. Various cell types may be used, such as kidney cells, fibroblasts, retinal cells, lung cells, etc. Examples of suitable hamster cells are the cell lines having the names BHK21 or HKCC. Suitable monkey cells are e.g. African green monkey cells, such as kidney cells as in the Vero cell line. Suitable dog cells are e.g. kidney cells, as in the MDCK cell line. Thus suitable cell lines include, but are not limited to: MDCK; CHO; 293T; BHK; Vero; MRC-5; PER.C6; WI-38; etc. Preferred mammalian cell lines for growing influenza viruses include: MDCK cells [28-31], derived from Madin Darby canine kidney; Vero cells [32-34], derived from African green monkey (*Cercopithecus aethiops*) kidney; or PER.C6 cells [35], derived from human embryonic retinoblasts. These cell lines are widely available e.g. from the American Type Cell Culture (ATCC) collection [36], from the Coriell Cell Repositories [37], or from the European Collection of Cell Cultures (ECACC). For example, the ATCC supplies various different Vero cells under catalog numbers CCL-81, CCL-81.2, CRL-1586 and CRL-1587, and it supplies MDCK cells under catalog number CCL-34. PER.C6 is available from the ECACC under deposit number 96022940. As a less-preferred alternative to mammalian cell lines, virus can be grown on avian cell lines [e.g. refs. 38-40], including cell lines derived from ducks (e.g. duck retina) or hens. Examples of avian cell lines include avian embryonic stem cells [38,41] and duck retina cells [39]. Suitable avian embryonic stem cells, include the EBx cell line derived from chicken embryonic stem cells, EB45, EB14, and EB14-074 [42]. Chicken embryo fibroblasts (CEF) may also be used.

The most preferred cell lines for growing influenza viruses are MDCK cell lines. The original MDCK cell line is available from the ATCC as CCL-34, but derivatives of this cell line may also be used. For instance, reference 28 discloses a MDCK cell line that was adapted for growth in suspension culture ('MDCK 33016', deposited as DSM ACC 2219). Similarly, reference 43 discloses a MDCK-derived cell line that grows in suspension in serum-free culture ('B-702', deposited as FERM BP-7449). Reference 44 discloses non-tumorigenic MDCK cells, including 'MDCK-S' (ATCC PTA-6500), 'MDCK-SF101' (ATCC PTA-6501), 'MDCK-SF102' (ATCC PTA-6502) and 'MDCK-SF103' (PTA-6503). Reference 45 discloses MDCK cell lines with high susceptibility to infection, including 'MDCK.5F1' cells (ATCC CRL-12042). Any of these MDCK cell lines can be used.

Where virus has been grown on a mammalian cell line then the composition will advantageously be free from egg proteins (e.g. ovalbumin and ovomucoid) and from chicken DNA, thereby reducing allergenicity.

Where virus has been grown on a cell line then the culture for growth, and also the viral inoculum used to start the culture, will preferably be free from (i.e. will have been tested for and given a negative result for contamination by) herpes simplex virus, respiratory syncytial virus, parainfluenza virus 3, SARS coronavirus, adenovirus, rhinovirus, reoviruses, polyomaviruses, birnaviruses, circoviruses, and/or parvoviruses [46]. Absence of herpes simplex viruses is particularly preferred.

For growth on a cell line, such as on MDCK cells, virus may be grown on cells in suspension [47-49] or in adherent culture. One suitable MDCK cell line for suspension culture is MDCK 33016 (deposited as DSM ACC 2219). As an alternative, microcarrier culture can be used.

Cell lines supporting influenza virus replication are preferably grown in serum-free culture media and/or protein free media. A medium is referred to as a serum-free medium in the context of the present invention in which there are no additives from serum of human or animal origin. Protein-free is understood to mean cultures in which multiplication of the cells occurs with exclusion of proteins, growth factors, other protein additives and non-serum proteins, but can optionally include proteins such as trypsin or other proteases that may be necessary for viral growth. The cells growing in such cultures naturally contain proteins themselves.

Cell lines supporting influenza virus replication are preferably grown below 37° C. [50] during viral replication e.g. 30-36° C.

The method for propagating virus in cultured cells generally includes the steps of inoculating the cultured cells with the strain to be cultured, cultivating the infected cells for a desired time period for virus propagation, such as for example as determined by virus titer or antigen expression (e.g. between 24 and 168 hours after inoculation) and collecting the propagated virus. The cultured cells are inoculated with a virus (measured by PFU or $TCID_{50}$) to cell ratio of 1:500 to 1:1, preferably 1:100 to 1:5, more preferably 1:50 to 1:10. The virus is added to a suspension of the cells or is applied to a monolayer of the cells, and the virus is absorbed on the cells for at least 60 minutes but usually less than 300 minutes, preferably between 90 and 240 minutes at 25° C. to 40° C., preferably 28° C. to 37° C. The infected cell culture (e.g. monolayers) may be removed either by freeze-thawing or by enzymatic action to increase the viral content of the harvested culture supernatants. The harvested fluids are then either inactivated or stored frozen. Cultured cells may be infected at a multiplicity of infection ("m.o.i.") of about 0.0001 to 10, preferably 0.002 to 5, more preferably to 0.001 to 2. Still more preferably, the cells are infected at a m.o.i of about 0.01. Infected cells may be harvested 30 to 60 hours post infection. Preferably, the cells are harvested 34 to 48 hours post infection. Still more preferably, the cells are harvested 38 to 40 hours post infection. Proteases (typically trypsin) are generally added during cell culture to allow viral release, and the proteases can be added at any suitable stage during the culture.

Haemagglutinin (HA) is the main immunogen in inactivated influenza vaccines, and vaccine doses are standardised by reference to HA levels, typically as measured by a single radial immunodiffusion (SRID) assay. Current vaccines typically contain about 15 µg of HA per strain, although lower doses are also used e.g. for children, or in pandemic situations. Fractional doses such as ½ (i.e. 7.5 µg HA per strain), ¼ and ½, have been used [51,52], as have higher doses (e.g. 3× or 9× doses [53,54]). Thus vaccines may include between 0.1 and 150 µg of HA per influenza strain, preferably between 0.1 and 50 µg e.g. 0.1-20 µg, 0.1-15 µg, 0.1-10 µg, 0.1-7.5 µg, 0.5-5 µg, etc. Particular doses include e.g. about 45, about 30, about 15, about 10, about 7.5, about 5, about 3.8, about 1.9, about 1.5, etc. µg per strain. These lower doses are most useful when an adjuvant is present in the vaccine, as with the invention.

For live vaccines, dosing is measured by median tissue culture infectious dose ($TCID_{50}$) rather than HA content, and a $TCID_{50}$ of between $10^6$ and $10^8$ (preferably between $10^{6.5}$-$10^{7.5}$) per strain is typical.

HA used with the invention may be a natural HA as found in a virus, or may have been modified. For instance, it is known to modify HA to remove determinants (e.g. hyperbasic regions around the cleavage site between HA1 and HA2) that cause a virus to be highly pathogenic in avian species, as these determinants can otherwise prevent a virus from being grown in eggs.

Compositions of the invention may include detergent e.g. a polyoxyethylene sorbitan ester surfactant (known as 'Tweens'), an octoxynol (such as octoxynol-9 (Triton X-100) or t-octylphenoxypolyethoxyethanol), a cetyl trimethyl ammonium bromide ('CTAB'), or sodium deoxycholate, particularly for a split or surface antigen vaccine. The detergent may be present only at trace amounts. Thus the vaccine may included less than 1 mg/ml of each of octoxynol-10, α-tocopheryl hydrogen succinate and polysorbate 80. Other residual components in trace amounts could be antibiotics (e.g. neomycin, kanamycin, polymyxin B).

An inactivated but non-whole cell vaccine (e.g. a split virus vaccine or a purified surface antigen vaccine) may include matrix protein, in order to benefit from the additional T cell epitopes that are located within this antigen. Thus a non-whole cell vaccine (particularly a split vaccine) that includes haemagglutinin and neuraminidase may additionally include M1 and/or M2 matrix protein, or fragment(s) thereof. Where a matrix protein is present, inclusion of detectable levels of M1 matrix protein is preferred. Nucleoprotein may also be present.

Host Cell DNA

Where virus has been grown on a cell line then it is standard practice to minimize the amount of residual cell line DNA in the final vaccine, in order to minimize any oncogenic activity of the DNA. Thus, where virus has been grown on a cell line, the composition preferably contains less than 10 ng (preferably less than 1 ng, and more preferably less than 100 pg) of residual host cell DNA per dose, although trace amounts of host cell DNA may be present. It is preferred that the average length of any residual host cell DNA is less than 500 bp e.g. less than 400 bp, less than 300 bp, less than 200 bp, less than 100 bp, etc. In general, the host cell DNA that it is desirable to exclude from compositions of the invention is DNA that is longer than 100 bp.

Measurement of residual host cell DNA is now a routine regulatory requirement for biologicals and is within the normal capabilities of the skilled person. The assay used to measure DNA will typically be a validated assay [55,56]. The performance characteristics of a validated assay can be described in mathematical and quantifiable terms, and its possible sources of error will have been identified. The assay will generally have been tested for characteristics such as accuracy, precision, specificity. Once an assay has been calibrated (e.g. against known standard quantities of host cell DNA) and tested then quantitative DNA measurements can be routinely performed. Three principle techniques for DNA quantification can be used: hybridization methods, such as Southern blots or slot blots [57]; immunoassay methods, such as the Threshold™ System [58]; and quantitative PCR [59]. These methods are all familiar to the skilled person, although the precise characteristics of each method may depend on the host cell in question e.g. the choice of probes for hybridization, the choice of primers and/or probes for amplification, etc. The Threshold™ system from Molecular Devices is a quantitative assay for picogram levels of total DNA, and has been used for monitoring levels of contaminating DNA in biopharmaceuticals [58]. A typical assay involves non-sequence-specific formation of a reaction complex between a biotinylated ssDNA binding protein, a urease-conjugated anti-ssDNA antibody, and. DNA. All assay components are included in the complete Total DNA Assay Kit available from the manufacturer. Various commercial manufacturers offer quantitative PCR assays for detecting residual host cell DNA e.g. AppTec™ Laboratory Services, BioReliance™, Althea Technologies, etc. A comparison of a chemiluminescent hybridisation assay and the total DNA Threshold™ system for measuring host cell DNA contamination of a human viral vaccine can be found in reference 60.

Contaminating DNA can be removed during vaccine preparation using standard purification procedures e.g. chromatography, etc. Removal of residual host cell DNA can be enhanced by nuclease treatment e.g. by using a DNase. A convenient method for reducing host cell DNA contamination is disclosed in references 61 & 62, involving a two-step treatment, first using a DNase (e.g. Benzonase), which may be used during viral growth, and then a cationic detergent (e.g. CTAB), which may be used during virion disruption. Treatment with an alkylating agent, such as β-propiolactone, can also be used to remove host cell DNA, and advantageously may also be used to inactivate virions [63].

Vaccines containing <10 ng (e.g. <1 ng, <100 pg) host cell DNA per 15 μg of haemagglutinin are preferred, as are vaccines containing <10 ng (e.g. <1 ng, <100 pg) host cell DNA per 0.25 ml volume. Vaccines containing <10 ng (e.g. <1 ng, <100 pg) host cell DNA per 50 μg of haemagglutinin are more preferred, as are vaccines containing <10 ng (e.g. <1 ng, <100 pg) host cell DNA per 0.5 ml volume.

The Adjuvant(s)

The invention involves the initial administration of an adjuvanted vaccine. Further vaccines may be unadjuvanted, or they may be adjuvanted but with a different adjuvant from the initial administration. The adjuvant(s) can function to enhance the immune responses (humoral and/or cellular) elicited in a patient who receives the composition.

Suitable adjuvants for use with the first vaccine, and for optional use with further vaccine dose(s), include, but are not limited to:

- A mineral-containing composition, including calcium salts and aluminum salts (or mixtures thereof). Calcium salts include calcium phosphate (e.g. the "CAP" particles disclosed in ref. 64). Aluminum salts include hydroxides, phosphates, sulfates, etc., with the salts taking any suitable form (e.g. gel, crystalline, amorphous, etc.). Adsorption to these salts is preferred. The mineral containing compositions may also be formulated as a particle of metal salt [65]. Aluminum salt adjuvants are described in more detail below.
- An oil-in-water emulsion, as described in more detail below.
- An immunostimulatory oligonucleotide, as described in more detail below.
- 3-O-deacylated monophosphoryl lipid A ('3dMPL', also known as 'MPL™'), as described in more detail below.
- An imidazoquinoline compound, such as Imiquimod ("R-837") [66,67], Resiquimod ("R-848") [68], and their analogs; and salts thereof (e.g. the hydrochloride salts). Further details about immunostimulatory imidazoquinolines can be found in references 69 to 73.
- A thiosemicarbazone compound, such as those disclosed in reference 74. Methods of formulating, manufacturing, and screening for active compounds are also described in reference 74. The thiosemicarbazones are particularly effective in the stimulation of human peripheral blood mononuclear cells for the production of cytokines, such as TNF-α.
- A nucleoside analog, such as: (a) Isatorabine (ANA-245; 7-thia-8-oxoguanosine):

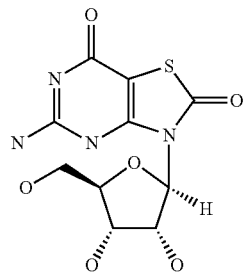 [SMILES: Nc1nc(=O)c2sc(=O)n([C@@H]3O[C@H](CO)[C@@H](O)[C@H]3O)c2[nH]1]

and prodrugs thereof; (b) ANA975; (c) ANA-025-1; (d) ANA380; (e) the compounds disclosed in references 75 to 77; (f) a compound having the formula:

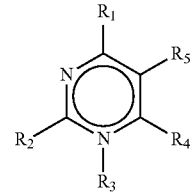

wherein:

$R_1$ and $R_2$ are each independently H, halo, $-NR_aR_b$, $-OH$, $C_{1-6}$ alkoxy, substituted $C_{1-6}$ alkoxy, heterocyclyl, substituted heterocyclyl, $C_{6-10}$ aryl, substituted $C_{6-10}$ aryl, $C_{1-6}$ alkyl, or substituted $C_{1-6}$ alkyl;

$R_3$ is absent, H, $C_{1-6}$ alkyl, substituted $C_{1-6}$ alkyl, $C_{6-10}$ aryl, substituted $C_{6-10}$ aryl, heterocyclyl, or substituted heterocyclyl;

$R_4$ and $R_5$ are each independently H, halo, heterocyclyl, substituted heterocyclyl, $-C(O)-R_d$, $C_{1-6}$ alkyl, substituted $C_{1-6}$ alkyl, or bound together to form a 5 membered ring as in $R_{4-5}$:

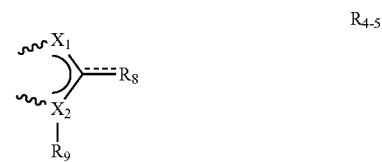

the binding being achieved at the bonds indicated by a ∼∼∼

$X_1$ and $X_2$ are each independently N, C, O, or S;

$R_8$ is H, halo, $-OH$, $C_{1-6}$ alkyl, $C_{2-6}$ alkenyl, $C_{2-6}$ alkynyl, $-OH$, $-NR_aR_b$, $-(CH_2)_n-O-R_c$, $-O-(C_{1-6}$ alkyl), $-S(O)_pR_e$, or $-C(O)-R_d$;

$R_9$ is H, $C_{1-6}$ alkyl, substituted $C_{1-6}$ alkyl, heterocyclyl, substituted heterocyclyl or $R_{9a}$, wherein $R_{9a}$ is:

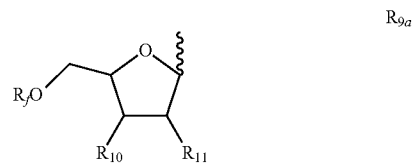

the binding being achieved at the bond indicated by a ∼∼∼

$R_{10}$ and $R_{11}$ are each independently H, halo, $C_{1-6}$ alkoxy, substituted $C_{1-6}$ alkoxy, $-NR_aR_b$, or $-OH$;

each $R_a$ and $R_b$ is independently H, $C_{1-6}$ alkyl, substituted $C_{1-6}$ alkyl, $-C(O)R_d$, $C_{6-10}$ aryl;

each $R_c$ is independently H, phosphate, diphosphate, triphosphate, $C_{1-6}$ alkyl, or substituted $C_{1-6}$ alkyl;

each $R_d$ is independently H, halo, $C_{1-6}$ alkyl, substituted $C_{1-6}$ alkyl, $C_{1-6}$ alkoxy, substituted $C_{1-6}$ alkoxy, $-NH_2$, $-NH(C_{1-6}$ alkyl), $-NH($substituted $C_{1-6}$ alkyl), $-N(C_{1-6}$ alkyl)$_2$, $-N($substituted $C_{1-6}$ alkyl)$_2$, $C_{6-10}$ aryl, or heterocyclyl;

each $R_e$ is independently H, $C_{1-6}$ alkyl, substituted $C_{1-6}$ alkyl, $C_{6-10}$ aryl, substituted $C_{6-10}$ aryl, heterocyclyl, or substituted heterocyclyl;

each $R_f$ is independently H, $C_{1-6}$ alkyl, substituted $C_{1-6}$ alkyl, $-C(O)R_d$, phosphate, diphosphate, or triphosphate;

each n is independently 0, 1, 2, or 3;
each p is independently 0, 1, or 2; or
or (g) a pharmaceutically acceptable salt of any of (a) to (f), a tautomer of any of (a) to (f), or a pharmaceutically acceptable salt of the tautomer.

A tryptanthrin compound, such as those disclosed in reference 78. Methods of formulating, manufacturing, and screening for active compounds are also described in reference 78. The thiosemicarbazones are particularly effective in the stimulation of human peripheral blood mononuclear cells for the production of cytokines, such as TNF-α.

Loxoribine (7-allyl-8-oxoguanosine) [79].

Compounds disclosed in reference 80, including: Acylpiperazine compounds, Indoledione compounds, Tetrahydraisoquinoline (THIQ) compounds, Benzocyclodione compounds, Aminoazavinyl compounds, Aminobenzimidazole quinolinone (ABIQ) compounds [81,82], Hydrapthalamide compounds, Benzophenone compounds, Isoxazole compounds, Sterol compounds, Quinazilinone compounds, Pyrrole compounds [83], Anthraquinone compounds, Quinoxaline compounds, Triazine compounds, Pyrazalopyrimidine compounds, and Benzazole compounds [84].

Compounds disclosed in reference 85, including 3,4-di (1H-indol-3-yl)-1H-pyrrole-2,5-diones, staurosporine analogs, derivatized pyridazines, chromen-4-ones, indolinones, quinazolines, and nucleoside analogs.

An aminoalkyl glucosaminide phosphate derivative, such as RC-529 [86,87].

A phosphazene, such as poly[di(carboxylatophenoxy) phosphazene] ("PCPP") as described, for example, in references 88 and 89.

Small molecule immunopotentiators (SMIPs) such as:
N2-methyl-1-(2-methylpropyl)-1H-irnidazo[4,5-c]quinoline-2,4-diamine
N2,N2-dimethyl-1-(2-methylpropyl)-1H-imidazo[4,5-c]quinoline-2,4-diamine
N2-ethyl-N2-methyl-1-(2-methylpropyl)-1H-imidazo[4,5-c]quinoline-2,4-diamine
N2-methyl-1-(2-methylpropyl)-N2-propyl-1H-imidazo[4,5-c]quinoline-2,4-diamine
1-(2-methylpropyl)-N2-propyl-1H-imidazo[4,5-c]quinoline-2,4-diamine
N2-butyl-1-(2-methylpropyl)-1H-imidazo[4,5-c]quinoline-2,4-diamine
N2-butyl-N2-methyl-1-(2-methylpropyl)-1H-imidazo[4,5-c]quinoline-2,4-diamine
N2-methyl-1-(2-methylpropyl)-N2-pentyl-1H-imidazo[4,5-c]quinoline-2,4-diamine
N2-methyl-1-(2-methylpropyl)-N2-prop-2-enyl-1H-imidazo[4,5-c]quinoline-2,4-diamine
1-(2-methylpropyl)-2-[(phenylmethyl)thio]-1H-imidazo[4,5-c]quinolin-4-amine
1-(2-methylpropyl)-2-(propylthio)-1H-imidazo[4,5-c]quinolin-4-amine
2-[[4-amino-1-(2-methylpropyl)-1H-imidazo[4,5-c]quinolin-2-yl](methyl)amino]ethanol
2-[[4-amino-1-(2-methylpropyl)-1H-imidazo[4,5-c]quinolin-2-yl](methyl)amino]ethyl acetate
4-amino-1-(2-methylpropyl)-1,3-dihydro-2H-imidazo[4,5-c]quinolin-2-one
N2-butyl-1-(2-methylpropyl)-N4,N4-bis(phenylmethyl)-1H-imidazo[4,5-c]quinoline-2,4-diamine
N2-butyl-N2-methyl-1-(2-methylpropyl)-N4,N4-bis(phenylmethyl)-1H-imidazo[4,5-c]quinoline-2,4-diamine
N2-methyl-1-(2-methylpropyl)-N4,N4-bis(phenylmethyl)-1H-imidazo[4,5-c]quinoline-2,4-diamine
N2,N2-dimethyl-1-(2-methylpropyl)-N4,N4-bis(phenylmethyl)-1H-imidazo[4,5-c]quinoline-2,4-diamine
1-{4-amino-2-[methyl(propyl)amino]-1H-imidazo[4,5-c]quinolin-1-yl}-2-methylpropan-2-ol
1-[4-amino-2-(propyl)amino)-1H-imidazo[4,5-c]quinolin-1-yl]-2-methylpropan-2-ol
N4,N4-dibenzyl-1-(2-methoxy-2-methylpropyl)-N2-propyl-1H-imidazo[4,5-c]quinoline-2,4-diamine.

Saponins [chapter 22 of ref. 131], which are a heterologous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as Stimulon™. Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in ref. 90. Saponin formulations may also comprise a sterol, such as cholesterol [91]. Combinations of saponins and cholesterols can be used to form unique particles called immunostimulating complexes (ISCOMs) [chapter 23 of ref. 131]. ISCOMs typically also include a phospholipid such as phosphatidylethanolamine or phosphatidylcholine. Any known saponin can be used in ISCOMs. Preferably, the ISCOM includes one or more of QuilA, QHA & QHC. ISCOMs are further described in refs. 91-93. Optionally, the ISCOMS may be devoid of additional detergent [94]. A review of the development of saponin based adjuvants can be found in refs. 95 & 96.

Bacterial ADP-ribosylating toxins (e.g. the *E. coli* heat labile enterotoxin "LT", cholera toxin "CT", or pertussis toxin "PT") and detoxified derivatives thereof, such as the mutant toxins known as LT-K63 and LT-R72 [97]. The use of detoxified ADP-ribosylating toxins as mucosal adjuvants is described in ref. 98 and as parenteral adjuvants in ref. 99.

Bioadhesives and mucoadhesives, such as esterified hyaluronic acid micro spheres [100] or chitosan and its derivatives [101].

Microparticles (i e. a particle of ~100 nm to ~150 μm in diameter, more preferably ~200 nm to ~30 μm in diameter, or ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) being preferred, optionally treated to have a negatively-charged surface (e.g. with SDS) or a positively-charged surface (e.g. with a cationic detergent, such as CTAB).

Liposomes (Chapters 13 & 14 of ref. 131). Examples of liposome formulations suitable for use as adjuvants are described in refs. 102-104.

Polyoxyethylene ethers and polyoxyethylene esters [105]. Such formulations further include polyoxyethylene sorbitan ester surfactants in combination with an octoxynol as well as polyoxyethylene alkyl ethers or ester surfactants in combination with at least one additional non-ionic surfactant such as an octoxynol [107]. Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

Muramyl peptides, such as N-acetylmuramyl-L-threonyl-D-isoglutamine ("thr-MDP"), N-acetyl-normuramyl-L-alanyl-D-isoglutamine (nor-MDP), N-acetylglucsaminyl-N-acetylmuramyl-L-Al-D-isoglu-L-Ala-dipalmitoxy propylamide ("DTP-DPP", or "Theramide™"), N-acetylmuramyl-L-alanyl-D-isoglutaminyl-L-alanine-2-(1'-2'dipalmitoyl-sn-glycero-3-hydroxyphosphoryloxy)-ethylamine ("MTP-PE").

An outer membrane protein proteosome preparation prepared from a first Gram-negative bacterium in combination with a liposaccharide (LPS) preparation derived from a second Gram-negative bacterium, wherein the outer membrane protein proteosome and LPS preparations form a stable non-covalent adjuvant complex. Such complexes include "IVX-908", a complex comprised of *Neisseria meningitidis* outer membrane and LPS. They have been used as adjuvants for influenza vaccines [108].

A polyoxidonium polymer [109,110] or other N-oxidized polyethylene-piperazine derivative.

Methyl inosine 5'-monophosphate ("MIMP") [111].

A polyhydroxlated pyrrolizidine compound [112], such as one having formula:

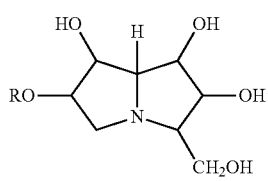

where R is selected from the group comprising hydrogen, straight or branched, unsubstituted or substituted, saturated or unsaturated acyl, alkyl (e.g. cycloalkyl), alkenyl, alkynyl and aryl groups, or a pharmaceutically acceptable salt or derivative thereof. Examples include, but are not limited to: casuarine, casuarine-6-α-D-glucopyranose, 3-epi-casuarine, 7-epi-casuarine, 3,7-diepi-casuarine, etc.

A CD1d ligand, such as an α-glycosylceramide [113-120] (e.g. α-galactosylceramide), phytosphingosine-containing α-glycosylceramides, OCH, KRN7000 [(2S,3S,4R)-1-O-(α-D-galactopyranosyl)-2-(N-hexacosanoylamino)-1,3,4-octadecanetriol], CRONY-101, 3"-O-sulfo-galactosylceramide, etc.

A gamma inulin [121] or derivative thereof, such as algammulin.

A compound of formula I, II or III, or a salt thereof:

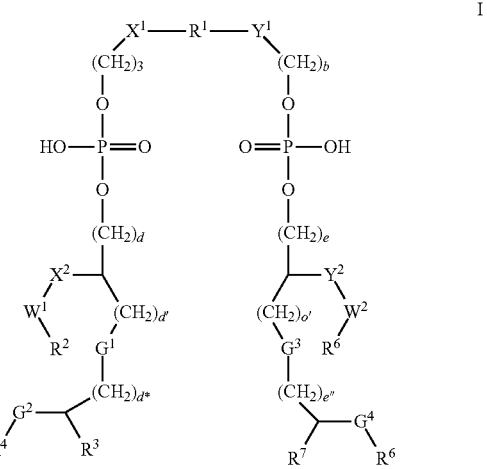

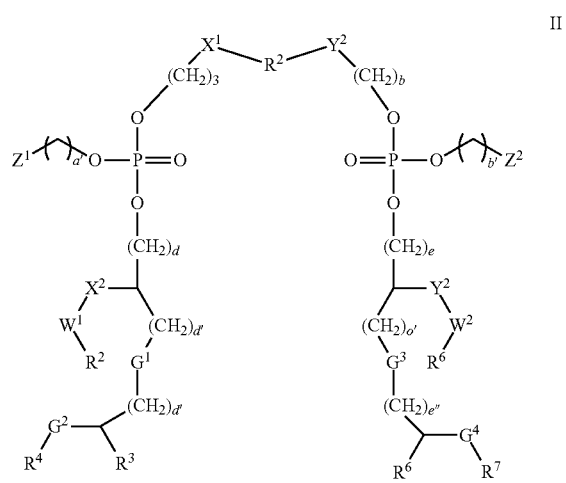

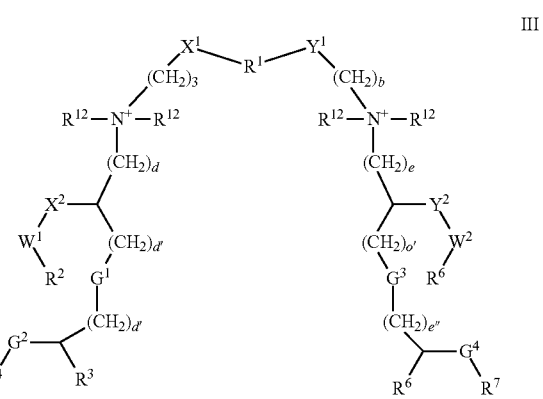

as defined in reference 122, such as 'ER 803058', 'ER 803732', 'ER 804053', ER 804058', 'ER 804059', 'ER 804442', 'ER 804680', 'ER 804764', ER 803022 or 'ER 804057' e.g.:

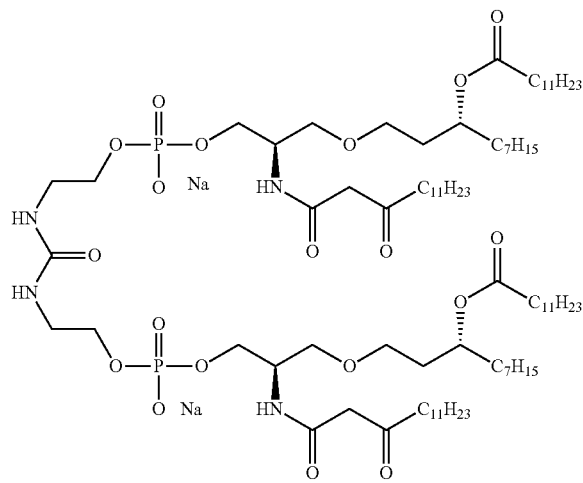

ER804057

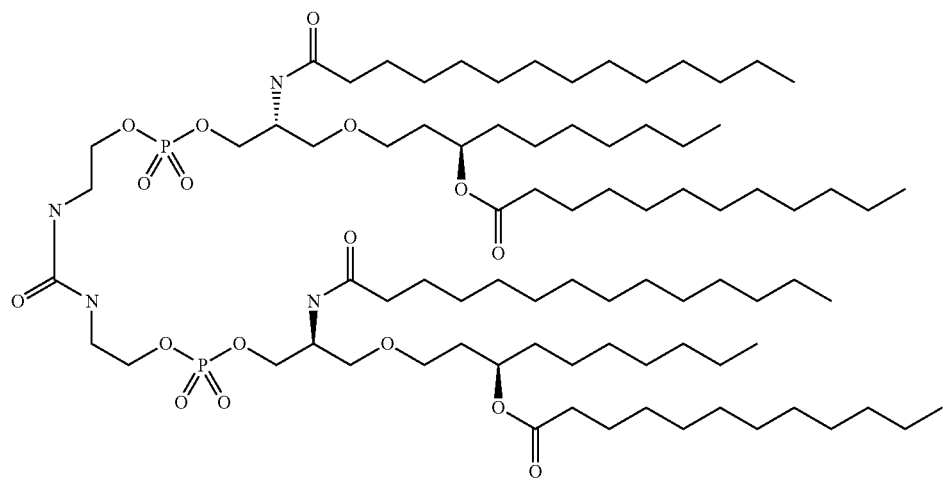

ER-803022

Derivatives of lipid A from *Escherichia coli* such as OM-174 (described in refs. 123 & 124).

A formulation of a cationic lipid and a (usually neutral) co-lipid, such as aminopropyl-dimethyl-myristoleyloxy-propanaminium bromide-diphytanoylphosphatidyl-ethanolamine ("Vaxfectin™") or aminopropyl-dimethyl-bis-dodecyloxy-propanaminium bromide-dioleoylphosphatidyl-ethanolamine ("GAP-DLRIE: DOPE"). Formulations containing (±)-N-(3-aminopropyl)-N,N-dimethyl-2,3-bis(syn-9-tetradeceneyloxy)-1-propanaminium salts are preferred [125].

Compounds containing lipids linked to a phosphate-containing acyclic backbone, such as the TLR4 antagonist E5564 [126,127]:

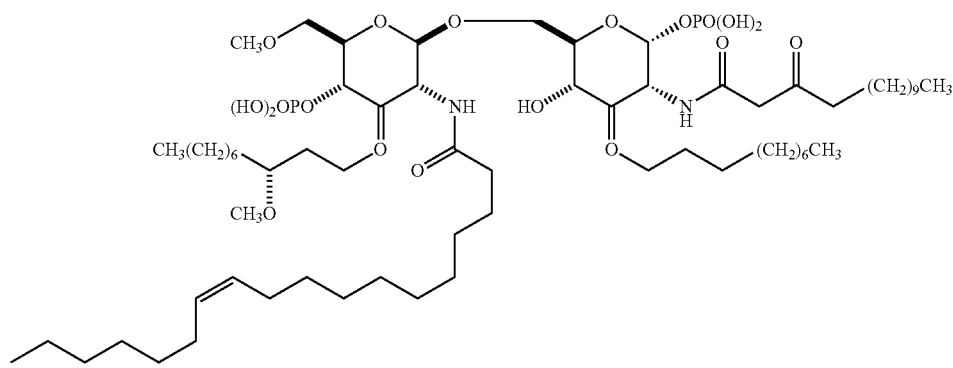

These and other adjuvant-active substances are discussed in more detail in references 131 & 132.

The adjuvant(s) for use in the present invention may be modulators and/or agonists of Toll-Like Receptors (TLR). For example, they may be agonists of one or more of the human TLR1, TLR2, TLR3, TLR4, TLR7, TLR8, and/or TLR9 proteins. Preferred agents are agonists of TLR7 (e.g. imidazoquinolines) and/or TLR9 (e.g. CpG oligonucleotides). These agents are useful for activating innate immunity pathways.

A single vaccine may include two or more of said adjuvants.

Antigens and adjuvants in a composition will typically be in admixture.

Aluminum Salt Adjuvants

The adjuvants known as aluminum hydroxide and aluminum phosphate may be used. These names are conventional, but are used for convenience only, as neither is a precise description of the actual chemical compound which is present (e.g. see chapter 9 of reference 131). The invention can use any of the "hydroxide" or "phosphate" adjuvants that are in general use as adjuvants.

The adjuvants known as "aluminium hydroxide" are typically aluminium oxyhydroxide salts, which are usually at least partially crystalline. Aluminium oxyhydroxide, which can be represented by the formula AlO(OH), can be distinguished from other aluminium compounds, such as aluminium hydroxide Al(OH)$_3$, by infrared (IR) spectroscopy, in particular by the presence of an adsorption band at 1070 cm$^{-1}$ and a strong shoulder at 3090-3100 cm$^{-1}$ [chapter 9 of ref. 131]. The degree of crystallinity of an aluminium hydroxide adjuvant is reflected by the width of the diffraction band at half height (WHH), with poorly-crystalline particles showing greater line broadening due to smaller crystallite sizes. The surface area increases as WHH increases, and adjuvants with higher WHH values have been seen to have greater capacity for antigen adsorption. A fibrous morphology (e.g. as seen in transmission electron micrographs) is typical for aluminium hydroxide adjuvants. The pI of aluminium hydroxide adjuvants is typically about 11 i.e. the adjuvant itself has a positive surface charge at physiological pH. Adsorptive capacities of between 1.8-2.6 mg protein per mg Al$^{+++}$ at pH 7.4 have been reported for aluminium hydroxide adjuvants.

The adjuvants known as "aluminium phosphate" are typically aluminium hydroxyphosphates, often also containing a small amount of sulfate (i.e. aluminium hydroxyphosphate sulfate). They may be obtained by precipitation, and the reaction conditions and concentrations during precipitation influence the degree of substitution of phosphate for hydroxyl in the salt. Hydroxyphosphates generally have a PO$_4$/Al molar ratio between 0.3 and 1.2. Hydroxyphosphates can be distinguished from strict AlPO$_4$ by the presence of hydroxyl groups. For example, an IR spectrum band at 3164 cm$^{-1}$ (e.g. when heated to 200° C.) indicates the presence of structural hydroxyls [ch. 9 of ref. 131]

The PO$_4$/Al$^{3+}$ molar ratio of an aluminium phosphate adjuvant will generally be between 0.3 and 1.2, preferably between 0.8 and 1.2, and more preferably 0.95±0.1. The aluminium phosphate will generally be amorphous, particularly for hydroxyphosphate salts. A typical adjuvant is amorphous aluminium hydroxyphosphate with PO$_4$/Al molar ratio between 0.84 and 0.92, included at 0.6 mg Al$^{3+}$/ml. The aluminium phosphate will generally be particulate (e.g. plate-like morphology as seen in transmission electron micrographs). Typical diameters of the particles are in the range 0.5-20 µm (e.g. about 5-10 µm) after any antigen adsorption. Adsorptive capacities of between 0.7-1.5 mg protein per mg Al$^{+++}$ at pH 7.4 have been reported for aluminium phosphate adjuvants.

The point of zero charge (PZC) of aluminium phosphate is inversely related to the degree of substitution of phosphate for hydroxyl, and this degree of substitution can vary depending on reaction conditions and concentration of reactants used for preparing the salt by precipitation. PZC is also altered by changing the concentration of free phosphate ions in solution (more phosphate=more acidic PZC) or by adding a buffer such as a histidine buffer (makes PZC more basic). Aluminium phosphates used according to the invention will generally have a PZC of between 4.0 and 7.0, more preferably between 5.0 and 6.5 e.g. about 5.7.

Suspensions of aluminium salts used to prepare compositions of the invention may contain a buffer (e.g. a phosphate or a histidine or a Tris buffer), but this is not always necessary. The suspensions are preferably sterile and pyrogen-free. A suspension may include free aqueous phosphate ions e.g. present at a concentration between 1.0 and 20 mM, preferably between 5 and 15 mM, and more preferably about 10 mM. The suspensions may also comprise sodium chloride.

The invention can use a mixture of both an aluminium hydroxide and an aluminium phosphate. In this case there may be more aluminium phosphate than hydroxide e.g. a weight ratio of at least 2:1 e.g. ≥5:1, ≥6:1, ≥7:1, ≥8:1, ≥9:1, etc.

The concentration of Al$^{+++}$ in a composition for administration to a patient is preferably less than 10 mg/ml e.g. ≤5 mg/ml, ≤4 mg/ml, ≤3 mg/ml, ≤2 mg/ml, ≤1 mg/ml, etc. A preferred range is between 0.3 and 1 mg/ml. A maximum of 0.85 mg/dose is preferred.

Oil-in-Water Emulsion Adjuvants

Oil-in-water emulsions have been found to be particularly suitable for use in adjuvanting influenza virus vaccines. Various such emulsions are known, and they typically include at least one oil and at least one surfactant, with the oil(s) and surfactant(s) being biodegradable (metabolisable) and biocompatible. The oil droplets in the emulsion are generally less than 5 µm in diameter, and may even have a sub-micron diameter, with these small sizes being achieved with a microfluidiser to provide stable emulsions. Droplets with a size less than 220 nm are preferred as they can be subjected to filter sterilization.

The invention can be used with oils such as those from an animal (such as fish) or vegetable source. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and may therefore be used in the practice of this invention. The procedures for separation, purification, saponification and other means necessary for obtaining pure oils from animal sources are well known in the art. Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoids known as squalene, 2,6,10,15,19,23-hexamethyl-2,6,10,14,18,22-tetracosahexaene, which is particularly preferred herein. Squalane, the saturated analog to squalene, is also a preferred oil. Fish oils, including squalene and squalane, are readily available from commercial sources or may be obtained by methods known in the art. Other preferred oils are the tocopherols (see below). Mixtures of oils can be used.

Surfactants can be classified by their 'HLB' (hydrophile/lipophile balance). Preferred surfactants of the invention have a HLB of at least 10, preferably at least 15, and more preferably at least 16. The invention can be used with surfactants including, but not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IG-EPAL CA-630/NP-40); phospholipids such as phosphatidylcholine (lecithin); nonylphenol ethoxylates, such as the Tergitol™ NP series; polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate. Non-ionic surfactants are preferred. Preferred surfactants for including in the emulsion are Tween 80 (polyoxyethylene sorbitan monooleate), Span 85 (sorbitan trioleate), lecithin and Triton X-100.

Mixtures of surfactants can be used e.g. Tween 80/Span 85 mixtures. A combination of a polyoxyethylene sorbitan ester such as polyoxyethylene sorbitan monooleate (Tween 80) and an octoxynol such as t-octylphenoxypolyethoxyethanol (Triton X-100) is also suitable. Another useful combination comprises laureth 9 plus a polyoxyethylene sorbitan ester and/or an octoxynol.

Preferred amounts of surfactants (% by weight) are: polyoxyethylene sorbitan esters (such as Tween 80) 0.01 to 1%, in particular about 0.1%; octyl- or nonylphenoxy polyoxyethanols (such as Triton X-100, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

Specific oil-in-water emulsion adjuvants useful with the invention include, but are not limited to:

A submicron emulsion of squalene, Tween 80, and Span 85. The composition of the emulsion by volume can be about 5% squalene, about 0.5% polysorbate 80 and about 0.5% Span 85. In weight terms, these ratios become 4.3% squalene, 0.5% polysorbate 80 and 0.48% Span 85. This adjuvant is known as 'MF59' [128-130], as described in more detail in Chapter 10 of ref. 131 and chapter 12 of ref. 132. The MF59 emulsion advantageously includes citrate ions e.g. 10 mM sodium citrate buffer.

An emulsion of squalene, a tocopherol, and Tween 80. The emulsion may include phosphate buffered saline. It may also include Span 85 (e.g. at 1%) and/or lecithin. These emulsions may have from 2 to 10% squalene, from 2 to 10% tocopherol and from 0.3 to 3% Tween 80, and the weight ratio of squalene:tocopherol is preferably ≤1 as this provides a more stable emulsion. Squalene and Tween 80 may be present volume ratio of about 5:2. One such emulsion can be made by dissolving Tween 80 in PBS to give a 2% solution, then mixing 90 ml of this solution with a mixture of (5 g of DL-α-tocopherol and 5 ml squalene), then microfluidising the mixture. The resulting emulsion may have submicron oil droplets e.g. with an average diameter of between 100 and 250 nm, preferably about 180 nm.

An emulsion of squalene, a tocopherol, and a Triton detergent (e.g. Triton X-100). The emulsion may also include a 3d-MPL (see below). The emulsion may contain a phosphate buffer.

An emulsion comprising a polysorbate (e.g. polysorbate 80), a Triton detergent (e.g. Triton X-100) and a tocopherol (e.g. an α-tocopherol succinate). The emulsion may include these three components at a mass ratio of about 75:11:10 (e.g. 750 μg/ml polysorbate 80, 110 μg/ml Triton X-100 and 100 μg/ml α-tocopherol succinate), and these concentrations should include any contribution of these components from antigens. The emulsion may also include squalene. The emulsion may also include a 3d-MPL (see below). The aqueous phase may contain a phosphate buffer.

An emulsion of squalane, polysorbate 80 and poloxamer 401 ("Pluronic™ L121"). The emulsion can be formulated in phosphate buffered saline, pH 7.4. This emulsion is a useful delivery vehicle for muramyl dipeptides, and has been used with threonyl-MDP in the "SAF-1" adjuvant [133] (0.05-1% Thr-MDP, 5% squalane, 2.5% Pluronic L121 and 0.2% polysorbate 80). It can also be used without the Thr-MDP, as in the "AF" adjuvant [134] (5% squalane, 1.25% Pluronic L121 and 0.2% polysorbate 80). Microfluidisation is preferred.

An emulsion comprising squalene, an aqueous solvent, a polyoxyethylene alkyl ether hydrophilic nonionic surfactant (e.g. polyoxyethylene (12) cetostearyl ether) and a hydrophobic nonionic surfactant (e.g. a sorbitan ester or mannide ester, such as sorbitan monoleate or 'Span 80'). The emulsion is preferably thermoreversible and/or has at least 90% of the oil droplets (by volume) with a size less than 200 nm [135]. The emulsion may also include one or more of alditol; a cryoprotective agent (e.g. a sugar, such as dodecylmaltoside and/or sucrose); and/or an alkylpolyglycoside. Such emulsions may be lyophilized.

An emulsion having from 0.5-50% of an oil, 0.1-10% of a phospholipid, and 0.05-5% of a non-ionic surfactant. As described in reference 136, preferred phospholipid components are phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.

A submicron oil-in-water emulsion of a non-metabolisable oil (such as light mineral oil) and at least one surfactant (such as lecithin, Tween 80 or Span 80). Additives may be included, such as QuilA saponin, cholesterol, a saponin-lipophile conjugate (such as GPI-0100, described in reference 137, produced by addition of aliphatic amine to desacylsaponin via the carboxyl group of glucuronic acid), dimethyldioctadecylammonium bromide and/or N,N-dioctadecyl-N,N-bis(2-hydroxyethyl)propanediamine.

An emulsion in which a saponin (e.g. QuilA or QS21) and a sterol (e.g. a cholesterol) are associated as helical micelles [138].

An emulsion comprising a mineral oil, a non-ionic lipophilic ethoxylated fatty alcohol, and a non-ionic hydrophilic surfactant (e.g. an ethoxylated fatty alcohol and/or polyoxyethylene-polyoxypropylene block copolymer) [139].

An emulsion comprising a mineral oil, a non-ionic hydrophilic ethoxylated fatty alcohol, and a non-ionic lipophilic surfactant (e.g. an ethoxylated fatty alcohol and/or polyoxyethylene-polyoxypropylene block copolymer) [139].

The emulsions may be mixed with antigen extemporaneously, at the time of delivery. Thus the adjuvant and antigen may be kept separately in a packaged or distributed vaccine, ready for final formulation at the time of use. The antigen will generally be in an aqueous form, such that the vaccine is finally prepared by mixing two liquids. The volume ratio of the two liquids for mixing can vary (e.g. between 5:1 and 1:5) but is generally about 1:1.

After the antigen and adjuvant have been mixed, haemagglutinin antigen will generally remain in aqueous solution but may distribute itself around the oil/water interface. In general, little if any haemagglutinin will enter the oil phase of the emulsion.

Where a composition includes a tocopherol, any of the a, $\beta$, $\gamma$, $\delta$, $\epsilon$ or $\xi$ tocopherols can be used, but $\alpha$-tocopherols are preferred. The tocopherol can take several forms e.g. different salts and/or isomers. Salts include organic salts, such as succinate, acetate, nicotinate, etc. D-$\alpha$-tocopherol and DL-$\alpha$-tocopherol can both be used. Tocopherols are advantageously included in vaccines for use in elderly patients (e.g. aged 60 years or older) because vitamin E has been reported to have a positive effect on the immune response in this patient group [140]. They also have antioxidant properties that may help to stabilize the emulsions [141]. A preferred $\alpha$-tocopherol is DL-$\alpha$-tocopherol, and the preferred salt of this tocopherol is the succinate. The succinate salt has been found to cooperate with TNF-related ligands in vivo. Moreover, $\alpha$-tocopherol succinate is known to be compatible with influenza vaccines and to be a useful preservative as an alternative to mercurial compounds [10].

Immunostimulatory Oligonucleotides

Immunostimulatory oligonucleotides can include nucleotide modifications/analogs such as phosphorothioate modifications and can be double-stranded or (except for RNA) single-stranded. References 142, 143 and 144 disclose possible analog substitutions e.g. replacement of guanosine with 2'-deoxy-7-deazaguanosine. The adjuvant effect of CpG oligonucleotides is further discussed in refs. 145-150. A CpG sequence may be directed to TLR9, such as the motif GTCGTT or TTCGTT [151]. The CpG sequence may be specific for inducing a Th1 immune response, such as a CpG-A ODN (oligodeoxynucleotide), or it may be more specific for inducing a B cell response, such a CpG-B ODN. CpG-A and CpG-B ODNs are discussed in refs. 152-154. Preferably, the CpG is a CpG-A ODN. Preferably, the CpG oligonucleotide is constructed so that the 5' end is accessible for receptor recognition. Optionally, two CpG oligonucleotide sequences may be attached at their 3' ends to form "immunomers". See, for example, references 151 & 155-157. A useful CpG adjuvant is CpG7909, also known as ProMune™ (Coley Pharmaceutical Group, Inc.).

As an alternative, or in addition, to using CpG sequences, TpG sequences can be used [158]. These oligonucleotides may be free from unmethylated CpG motifs.

The immunostimulatory oligonucleotide may be pyrimidine-rich. For example, it may comprise more than one consecutive thymidine nucleotide (e.g. TTTT, as disclosed in ref. 158), and/or it may have a nucleotide composition with >25% thymidine (e.g. >35%, >40%, >50%, >60%, >80%, etc.). For example, it may comprise more than one consecutive cytosine nucleotide (e.g. CCCC, as disclosed in ref. 158), and/or it may have a nucleotide composition with >25% cytosine (e.g. >35%, >40%, >50%, >60%, >80%, etc.). These oligonucleotides may be free from unmethylated CpG motifs.

Immunostimulatory oligonucleotides will typically comprise at least 20 nucleotides. They may comprise fewer than 100 nucleotides.

3 de-O-acylated monophosphoryl Lipid A

3dMPL (also known as 3 de-O-acylated monophosphoryl lipid A or 3-O-desacyl-4'-monophosphoryl lipid A) is an adjuvant in which position 3 of the reducing end glucosamine in monophosphoryl lipid A has been de-acylated. 3dMPL has been prepared from a heptoseless mutant of *Salmonella minnesota*, and is chemically similar to lipid A but lacks an acid-labile phosphoryl group and a base-labile acyl group. It activates cells of the monocyte/macrophage lineage and stimulates release of several cytokines, including IL-1, IL-12, TNF-$\alpha$ and GM-CSF (see also ref. 159). Preparation of 3dMPL was originally described in reference 160.

3dMPL can take the form of a mixture of related molecules, varying by their acylation (e.g. having 3, 4, 5 or 6 acyl chains, which may be of different lengths). The two glucosamine (also known as 2-deoxy-2-amino-glucose) monosaccharides are N-acylated at their 2-position carbons (i.e. at positions 2 and 2'), and there is also O-acylation at the 3' position. The group attached to carbon 2 has formula —NH—CO—CH$_2$—CR$^1$R$^{1'}$. The group attached to carbon 2' has formula —NH—CO—CH$_2$—CR$^2$R$^{2'}$. The group attached to carbon 3' has formula —O—CO—CH$_2$—CR$^3$R$^{3'}$. A representative structure is:

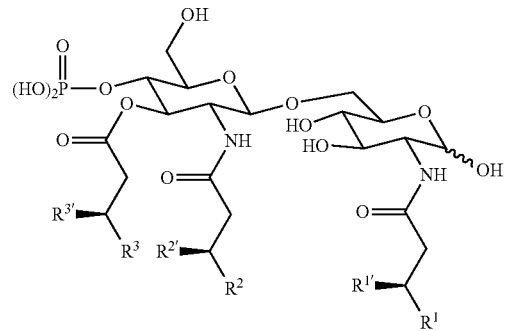

Groups R$^1$, R$^2$ and R$^3$ are each independently —(CH$_2$)$_n$—CH$_3$. The value of n is preferably between 8 and 16, more preferably between 9 and 12, and is most preferably 10.

Groups R$^{1'}$, R$^{2'}$ and R$^{3'}$ can each independently be: (a) —H; (b) —OH; or (c) —O—CO—R$^4$, where R$^4$ is either —H or —(CH$_2$)$_m$—CH$_3$, wherein the value of m is preferably between 8 and 16, and is more preferably 10, 12 or 14. At the 2 position, m is preferably 14. At the 2' position, m is preferably 10. At the 3' position, m is preferably 12. Groups R$^{1'}$, R$^{2'}$ and R$^{3'}$ are thus preferably —O-acyl groups from dodecanoic acid, tetradecanoic acid or hexadecanoic acid.

When all of R $R^{1'}$, $R^{2'}$ and $R^{3'}$ are —H then the 3dMPL has only 3 acyl chains (one on each of positions 2, 2' and 3'). When only two of $R^{1'}$, $R^{2'}$ and $R^{3'}$ are —H then the 3dMPL can have 4 acyl chains. When only one of $R^{1'}$, $R^{2'}$ and $R^{3'}$ is —H then the 3dMPL can have 5 acyl chains. When none of $R^{1'}$, $R^{2'}$ and $R^{3'}$ is —H then the 3dMPL can have 6 acyl chains. The 3dMPL adjuvant used according to the invention can be a mixture of these forms, with from 3 to 6 acyl chains, but it is preferred to include 3dMPL with 6 acyl chains in the mixture, and in particular to ensure that the hexaacyl chain form makes up at least 10% by weight of the total 3dMPL e.g. ≥20%, ≥30%, ≥40%, ≥50% or more. 3dMPL with 6 acyl chains has been found to be the most adjuvant-active form.

Thus the most preferred form of 3dMPL for inclusion in compositions of the invention is:

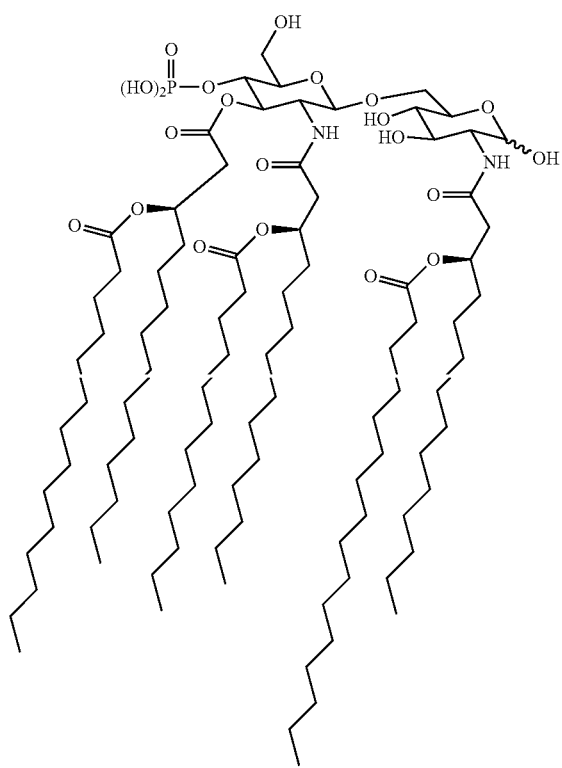

Where 3dMPL is used in the form of a mixture then references to amounts or concentrations of 3dMPL in compositions of the invention refer to the combined 3dMPL species in the mixture.

In aqueous conditions, 3dMPL can form micellar aggregates or particles with different sizes e.g. with a diameter <150 nm or >500 nm. Either or both of these can be used with the invention, and the better particles can be selected by routine assay. Smaller particles (e.g. small enough to give a clear aqueous suspension of 3dMPL) are preferred for use according to the invention because of their superior activity [161]. Preferred particles have a mean diameter less than 220 nm, more preferably less than 200 nm or less than 150 nm or less than 120 nm, and can even have a mean diameter less than 100 nm. In most cases, however, the mean diameter will not be lower than 50 nm. These particles are small enough to be suitable for filter sterilization. Particle diameter can be assessed by the routine technique of dynamic light scattering, which reveals a mean particle diameter. Where a particle is said to have a diameter of x nm, there will generally be a distribution of particles about this mean, but at least 50% by number (e.g. ≥60%, ≥70%, ≥80%, ≥90%, or more) of the particles will have a diameter within the range x±25%.

3dMPL can advantageously be used in combination with an oil-in-water emulsion. Substantially all of the 3dMPL may be located in the aqueous phase of the emulsion.

The 3dMPL can be used on its own, or in combination with one or more further compounds. For example, it is known to use 3dMPL in combination with the QS21 saponin (including in an oil-in-water emulsion [163]), with an immunostimulatory oligonucleotide, with both QS21 and an immunostimulatory oligonucleotide, with aluminum phosphate [164], with aluminum hydroxide [165], or with both aluminum phosphate and aluminum hydroxide.

Preferred Adjuvanting Regimens

Dosing regimens of the invention involve an initial administration of an adjuvanted influenza vaccine. Preferred adjuvants for use in this initial vaccine are oil-in-water emulsions.

The second dose of a 2-dose regimen is preferably unadjuvanted. As an alternative, it may be adjuvanted, but with a different adjuvant from the first dose. Where the first dose is adjuvanted with an oil-in-water emulsion, a preferred adjuvant for use with an adjuvanted second dose comprises an aluminium salt.

Pharmaceutical Compositions

Compositions of the invention are pharmaceutically acceptable and are typically in aqueous form. They may include components in addition to the antigen (and, where applicable, the adjuvant) e.g. they typically include one or more pharmaceutical carrier(s) and/or excipient(s). A thorough discussion of such components is available in reference 166.

The composition may include preservatives such as thiomersal or 2-phenoxyethanol. It is preferred, however, that the vaccine should be substantially free from (i.e. less than 5 μg/ml) mercurial material e.g. thiomersal-free [10,167]. Vaccines containing no mercury are more preferred. Preservative-free vaccines are particularly preferred.

To control tonicity, it is preferred to include a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate dehydrate, magnesium chloride, calcium chloride, etc.

Compositions will generally have an osmolality of between 200 mOsm/kg and 400 mOsm/kg, preferably between 240-360 mOsm/kg, and will more preferably fall within the range of 290-310 mOsm/kg. Osmolality has previously been reported not to have an impact on pain caused by vaccination [168], but keeping osmolality in this range is nevertheless preferred.

Compositions may include one or more buffers. Typical buffers include: a phosphate buffer; a Tris buffer; a borate buffer; a succinate buffer; a histidine buffer (particularly with an aluminum hydroxide adjuvant); or a citrate buffer. Buffers will typically be included in the 5-20 mM range.

The pH of a composition will generally be between 5.0 and 8.1, and more typically between 6.0 and 8.0 e.g. between 6.5 and 7.5, between 7.0 and 7.8. A process of the invention may therefore include a step of adjusting the pH of the bulk vaccine prior to packaging.

The composition is preferably sterile. The composition is preferably non-pyrogenic e.g. containing <1 EU (endotoxin unit, a standard measure) per dose, and preferably <0.1 EU per dose. The composition is preferably gluten free.

The composition may include material for a single immunisation, or may include material for multiple immunisations (i.e. a 'multidose' kit). The inclusion of a preservative is preferred in multidose arrangements. As an alternative (or in addition) to including a preservative in multidose compositions, the compositions may be contained in a container having an aseptic adaptor for removal of material.

Influenza vaccines are typically administered in a dosage volume of about 0.5 ml, although a half dose (i.e. about 0.25 ml) may be administered to children (e.g. up to 36 months of age).

Compositions and kits are preferably stored at between 2° C. and 8° C. They should not be frozen. They should ideally be kept out of direct light.

Kits of the Invention

The invention includes kits of the first and further influenza vaccines. One kit component will be a first adjuvanted vaccine, and another kit component will be a further vaccine, optionally adjuvanted. The two components will be kept separately, as they are administered to a patient at substantially different times.

Each individual vaccine in a kit may be ready for use, or may be ready for extemporaneous preparation at the time of delivery. This extemporaneous arrangement allows the adjuvant and the antigen to be kept separately until the time of use, which is particularly useful when using an oil-in-water emulsion adjuvant.

Where a vaccine is prepared extemporaneously, its components are physically separate from each other within the kit, and this separation can be achieved in various ways. For instance, the two components may be in two separate containers, such as vials. The contents of the two vials can then be mixed e.g. by removing the contents of one vial and adding them to the other vial, or by separately removing the contents of both vials and mixing them in a third container. In a preferred arrangement, one of the kit components is in a syringe and the other is in a container such as a vial. The syringe can be used (e.g. with a needle) to insert its contents into the second container for mixing, and the mixture can then be withdrawn into the syringe. The mixed contents of the syringe can then be administered to a patient, typically through a new sterile needle. Packing one component in a syringe eliminates the need for using a separate syringe for patient administration.

In another preferred arrangement, the two components of a vaccine are held together but separately in the same syringe e.g. a dual-chamber syringe, such as those disclosed in references 169-176 etc. When the syringe is actuated (e.g. during administration to a patient) then the contents of the two chambers are mixed. This arrangement avoids the need for a separate mixing step at the time of use.

Where a vaccine is prepared extemporaneously, its components will generally be in aqueous form. In some arrangements, a component (typically the antigen component rather than the adjuvant component) is in dry form (e.g. in a lyophilised form), with the other component being in aqueous form. The two components can be mixed in order to reactivate the dry component and give an aqueous composition for administration to a patient. A lyophilised component will typically be located within a vial rather than a syringe. Dried components may include stabilizers such as lactose, sucrose or mannitol, as well as mixtures thereof e.g. lactose/sucrose mixtures, sucrose/mannitol mixtures, etc. One possible arrangement uses an aqueous adjuvant component in a pre-filled syringe and a lyophilised antigen component in a vial.

Packaging of Compositions or Kit Components

Suitable containers for compositions of the invention (or kit components) include vials, syringes (e.g. disposable syringes), nasal sprays, etc. These containers should be sterile.

Where a composition/component is located in a vial, the vial is preferably made of a glass or plastic material. The vial is preferably sterilized before the composition is added to it. To avoid problems with latex-sensitive patients, vials are preferably sealed with a latex-free stopper, and the absence of latex in all packaging material is preferred. The vial may include a single dose of vaccine, or it may include more than one dose (a 'multidose' vial) e.g. 10 doses. Preferred vials are made of colorless glass.

A vial can have a cap (e.g. a Luer lock) adapted such that a pre-filled syringe can be inserted into the cap, the contents of the syringe can be expelled into the vial (e.g. to reconstitute lyophilised material therein), and the contents of the vial can be removed back into the syringe. After removal of the syringe from the vial, a needle can then be attached and the composition can be administered to a patient. The cap is preferably located inside a seal or cover, such that the seal or cover has to be removed before the cap can be accessed. A vial may have a cap that permits aseptic removal of its contents, particularly for multidose vials.

Where a composition/component is packaged into a syringe, the syringe may have a needle attached to it. If a needle is not attached, a separate needle may be supplied with the syringe for assembly and use. Such a needle may be sheathed. Safety needles are preferred. 1-inch 23-gauge, 1-inch 25-gauge and ⅝-inch 25-gauge needles are typical. Syringes may be provided with peel-off labels on which the lot number, influenza season and expiration date of the contents may be printed, to facilitate record keeping. The plunger in the syringe preferably has a stopper to prevent the plunger from being accidentally removed during aspiration. The syringes may have a latex rubber cap and/or plunger. Disposable syringes contain a single dose of vaccine. The syringe will generally have a tip cap to seal the tip prior to attachment of a needle, and the tip cap is preferably made of a butyl rubber. If the syringe and needle are packaged separately then the needle is preferably fitted with a butyl rubber shield. Preferred syringes are those marketed under the trade name "Tip-Lok"™.

Containers may be marked to show a half-dose volume e.g. to facilitate delivery to children. For instance, a syringe containing a 0.5 ml dose may have a mark showing a 0.25 ml volume.

Where a glass container (e.g. a syringe or a vial) is used, then it is preferred to use a container made from a borosilicate glass rather than from a soda lime glass.

A kit or composition may be packaged (e.g. in the same box) with a leaflet including details of the vaccine e.g. instructions for administration, details of the antigens within the vaccine, etc. The instructions may also contain warnings e.g. to keep a solution of adrenaline readily available in case of anaphylactic reaction following vaccination, etc.

Methods of Treatment, and Administration of the Vaccine

Compositions of the invention are suitable for administration to human patients. The immune response raised according to the invention will generally include an antibody response, preferably a protective antibody response. Methods for assessing antibody responses, neutralising capability and protection after influenza virus vaccination are well known in the art. Human studies have shown that antibody titers against hemagglutinin of human influenza virus are correlated with protection (a serum sample hemagglutination-inhibition titer of about 30-40 gives around 50% protection from infection by a homologous virus) [177]. Antibody responses are typically measured by hemagglutination inhibition, by microneutralisation, by single radial immunodiffusion (SRID), and/or by single radial hemolysis (SRH). These assay techniques are well known in the art.

Compositions of the invention can be administered in various ways. The most preferred immunisation route is by intramuscular injection (e.g. into the arm or leg), but other available routes include subcutaneous injection, intranasal [178-180], oral [181], intradermal [182,183], transcutaneous, transdermal [184], etc.

Vaccines of the invention may be used to treat both children and adults. Influenza vaccines are currently recommended for use in pediatric and adult immunisation, from the age of 6 months. Thus the patient may be less than 1 year old, 1-5 years old, 5-15 years old, 15-55 years old, or at least 55 years old. Preferred patients for receiving the vaccines are the elderly (e.g. ≥50 years old, ≥60 years old, preferably ≥65 years), the young (e.g. ≤5 years old), hospitalised patients, healthcare workers, armed service and military personnel, pregnant women, the chronically ill, immunodeficient patients, patients who have taken an antiviral compound (e.g. an oseltamivir or zanamivir compound; see below) in the 7 days prior to receiving the vaccine, people with egg allergies and people travelling abroad. The vaccines are not suitable solely for these groups, however, and may be used more generally in a population. For pandemic strains, administration to all age groups is preferred.

Preferred compositions of the invention satisfy 1, 2 or 3 of the CPMP criteria for efficacy. In adults (18-60 years), these criteria are: (1) ≥70% seroprotection; (2) ≥40% seroconversion; and/or (3) a GMT increase of ≥2.5-fold. In elderly (>60 years), these criteria are: (1) ≥60% seroprotection; (2) ≥30% seroconversion; and/or (3) a GMT increase of ≥2-fold. These criteria are based on open label studies with at least 50 patients.

Treatment is by a multiple dose schedule. As mentioned above, the various doses will typically use the same form of antigen and share at least one common hemagglutinin subtype. It is preferred that the doses are either all given parenterally or all given mucosally. The doses will typically be given by the same administration route e.g. by the same parenteral route, such as i.m. injection.

The multiple doses will typically be administered at least 1 week apart (e.g. at least about 2 weeks, about 3 weeks, about 4 weeks, about 6 weeks, about 8 weeks, about 10 weeks apart, about 12 weeks, about 16 weeks apart, etc.).

Preferred dosing regimens of the invention are 2-dose regimens. Further doses may be administered in subsequent influenza seasons, typically in the usual 1-dose format, but the standard immunization in a single season (e.g. within a single 6 month period or 12 month period) according to the invention will involve 2 doses. Extra doses in the regimen (e.g. a 3-dose or a 4-dose regimen) are not preferred because of the extra antigen requirements. If a 3rd dose is included in the regimen, however, then the third dose may either be a repeat of the first dose, followed by the further dose, or it may be a repeat of the further dose e.g. an 'adjuvanted, adjuvanted, un-adjuvanted' regimen, or an 'adjuvanted, un-adjuvanted, un-adjuvanted' regimen.

Vaccines produced by the invention may be administered to patients at substantially the same time as (e.g. during the same medical consultation or visit to a healthcare professional or vaccination centre) other vaccines e.g. at substantially the same time as a measles vaccine, a mumps vaccine, a rubella vaccine, a MMR vaccine, a varicella vaccine, a MMRV vaccine, a diphtheria vaccine, a tetanus vaccine, a pertussis vaccine, a DTP vaccine, a conjugated *H. influenzae* type b vaccine, an inactivated poliovirus vaccine, a hepatitis B virus vaccine, a meningococcal conjugate vaccine (such as a tetravalent A-C-W135-Y vaccine), a respiratory syncytial virus vaccine, a pneumococcal conjugate vaccine, etc. Administration at substantially the same time as a pneumococcal vaccine or a meningococcal vaccine is particularly useful in elderly patients.

Similarly, vaccines of the invention may be administered to patients at substantially the same time as (e.g. during the same medical consultation or visit to a healthcare professional) an antiviral compound, and in particular an antiviral compound active against influenza virus (e.g. oseltamivir and/or zanamivir). These antivirals include neuraminidase inhibitors, such as a (3R,4R,5S)-4-acetylamino-5-amino-3 (1-ethylpropoxy)-1-cyclohexene-1-carboxylic acid or 5-(acetylamino)-4-[(aminoiminomethyl)-amino]-2,6-anhydro-3,4,5-trideoxy-D-glycero-D-galactonon-2-enonic acid, including esters thereof (e.g. the ethyl esters) and salts thereof (e.g. the phosphate salts). A preferred antiviral is (3R,4R,5S)-4-acetylamino-5-amino-3(1-ethylpropoxy)-1-cyclohexene-1-carboxylic acid, ethyl ester, phosphate (1:1), also known as oseltamivir phosphate (TAMIFLU™).

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x±10%.

Unless specifically stated, a process comprising a step of mixing two or more components does not require any specific order of mixing. Thus components can be mixed in any order. Where there are three components then two components can be combined with each other, and then the combination may be combined with the third component, etc.

Where animal (and particularly bovine) materials are used in the culture of cells, they should be obtained from sources that are free from transmissible spongiform encephalopathies (TSEs), and in particular free from bovine spongiform encephalopathy (BSE). Overall, it is preferred to culture cells in the total absence of animal-derived materials.

Where a compound is administered to the body as part of a composition then that compound may alternatively be replaced by a suitable prodrug.

Where a cell substrate is used for reassortment or reverse genetics procedures, it is preferably one that has been approved for use in human vaccine production e.g. as in Ph Eur general chapter 5.2.3.

BRIEF DESCRIPTION OF DRAWINGS

FIG. 1 shows anti-HA IgG ELISA responses in mice receiving various influenza vaccines.

MODES FOR CARRYING OUT THE INVENTION

Hemagglutinin was prepared from a H5N1 strain of avian influenza and was formulated for intramuscular injection at 0.2 µg per dose (50 µl volume per dose). Two vaccines were prepared: the first was unadjuvanted; the second was adjuvanted with MF59 emulsion at a 1:1 volume ratio. Vaccines were administered to four groups of female Balb/c mice, 8 weeks of age, at days 0 & 28. Mice were bled at days 14 and 42 and anti-HA immune responses were assessed by ELISA.

Results were as follows (see also FIG. 1):

|  | Group | | | |
| --- | --- | --- | --- | --- |
|  | A | B | C | D |
| Day 0 | No adjuvant | MF59 | No adjuvant | MF59 |
| Day 28 | No adjuvant | No adjuvant | MF59 | MF59 |
| Titre (day 14) | 13 | 313 | 6 | 271 |
| Responders | 3/10 | 10/10 | 3/10 | 10/10 |
| Titre (day 42) | 7125 | 75922 | 42219 | 148831 |
| Responders | 10/10 | 10/10 | 10/10 | 10/10 |

Thus the adjuvant significantly enhances the number of responders after the first immunization (compare groups A and B). Including adjuvant in either or both of the doses gave an anti-HA specific antibody response that is significantly higher than that induced by two doses of non-adjuvanted vaccine (compare groups B, C & D against group A). Moreover, animals primed with an adjuvanted vaccine can be boosted by a non-adjuvanted vaccine, achieving higher titers than priming with an unadjuvanted vaccine and boosting with an adjuvanted vaccine (compare groups B & C). Although the absolute titers were lower in group B than in group D, the response was more than adequate. Thus stocks of an adjuvant can be maintained by using it in only the first dose in a 2-dose regimen.

It will be understood that the invention has been described by way of example only and modifications may be made whilst remaining within the scope and spirit of the invention.

REFERENCES

The Contents of which are Hereby Incorporated by Reference

[1] Holmes et al. (2005) *Science* 309:989.
[2] Guy et al. (1998) *Clin Diagn Lab Immunol* 5:732-6.
[3] WO96/37624.
[4] WO98/46262.
[5] WO95/18861.
[6] WO02/28422.
[7] WO02/067983.
[8] WO02/074336.
[9] WO01/21151.
[10] WO02/097072.
[11] WO2005/113756.
[12] Huckriede et al. (2003) *Methods Enzymol* 373:74-91.
[13] Herlocher et al. (2004) *J Infect Dis* 190(9):1627-30.
[14] Le et al. (2005) *Nature* 437(7062):1108.
[15] World Health Organisation (2005) *Emerging Infectious Diseases* 11(10):1515-21.
[16] Hoffmann et al. (2002) *Vaccine* 20:3165-3170.
[17] Subbarao et al. (2003) *Virology* 305:192-200.
[18] Liu et al. (2003) *Virology* 314:580-590.
[19] Ozaki et al. (2004) *J. Virol.* 78:1851-1857.
[20] Webby et al. (2004) *Lancet* 363:1099-1103.
[21] WO00/60050.
[22] WO01/04333.
[23] U.S. Pat. No. 6,649,372.
[24] Neumann et al. (2005) *Proc Natl Acad Sci USA* 102:16825-9.
[25] WO2006/067211.
[26] WO01/83794.
[27] Hoffmann et al. (2000) *Virology* 267(2):310-7.
[28] WO97/37000.
[29] Brands et al. (1999) *Dev Biol Stand* 98:93-100.
[30] Halperin et al. (2002) *Vaccine* 20:1240-7.
[31] Tree et al. (2001) *Vaccine* 19:3444-50.
[32] Kistner et al. (1998) *Vaccine* 16:960-8.
[33] Kistner et al. (1999) *Dev Biol Stand* 98:101-110.
[34] Bruhl et al. (2000) *Vaccine* 19:1149-58.
[35] Pau et al. (2001) *Vaccine* 19:2716-21.
[36] http://www.atcc.org/
[37] http://locus.umdnj.edu/
[38] WO03/076601.
[39] WO2005/042728.
[40] WO03/043415.
[41] WO01/85938.
[42] WO2006/108846.
[43] EP-A-1260581 (WO01/64846).
[44] WO2006/071563.
[45] WO2005/113758.
[46] WO2006/027698.
[47] WO97/37000
[48] WO03/023021
[49] WO03/023025
[50] WO97/37001.
[51] WO01/22992.
[52] Hehme et al. (2004) *Virus Res.* 103(1-2):163-71.
[53] Treanor et al. (1996) *J Infect Dis* 173:1467-70.
[54] Keitel et al. (1996) *Clin Diagn Lab Immunol* 3:507-10.
[55] Lundblad (2001) *Biotechnology and Applied Biochemistry* 34:195-197.
[56] *Guidance for Industry: Bioanalytical Method Validation.* U.S. Department of Health and Human Services Food and Drug Administration Center for Drug Evaluation and Research (CDER) Center for Veterinary Medicine (CVM). May 2001.
[57] Ji et al. (2002) *Biotechniques.* 32:1162-7.
[58] Briggs (1991) *J Parenter Sci Technol.* 45:7-12.
[59] Lahijani et al. (1998) *Hum Gene Ther.* 9:1173-80.
[60] Lokteff et al. (2001) *Biologicals.* 29:123-32.
[61] EP-B-0870508.
[62] U.S. Pat. No. 5,948,410.
[63] WO2007/052163.
[64] U.S. Pat. No. 6,355,271.
[65] WO00/23105.
[66] U.S. Pat. No. 4,680,338.
[67] U.S. Pat. No. 4,988,815.
[68] WO92/15582.
[69] Stanley (2002) *Clin Exp Dermatol* 27:571-577.
[70] Wu et al. (2004) *Antiviral Res.* 64(2):79-83.
[71] Vasilakos et al. (2000) *Cell Immunol.* 204(1):64-74.
[72] U.S. Pat. Nos. 4,689,338, 4,929,624, 5,238,944, 5,266,575, 5,268,376, 5,346,905, 5,352,784, 5,389,640, 5,395,937, 5,482,936, 5,494,916, 5,525,612, 6,083,505, 6,440,992, 6,627,640, 6,656,938, 6,660,735, 6,660,747, 6,664,260, 6,664,264, 6,664,265, 6,667,312, 6,670,372, 6,677,347, 6,677,348, 6,677,349, 6,683,088, 6,703,402, 6,743,920, 6,800,624, 6,809,203, 6,888,000 and 6924293.
[73] Jones (2003) *Curr Opin Investig Drugs* 4:214-218.
[74] WO2004/060308.
[75] U.S. Pat. No. 6,924,271.
[76] US2005/0070556.
[77] U.S. Pat. No. 5,658,731.
[78] WO2004/064759.

[79] U.S. Pat. No. 5,011,828.
[80] WO2004/87153.
[81] U.S. Pat. No. 6,605,617.
[82] WO02/18383.
[83] WO2004/018455.
[84] WO03/082272.
[85] WO2006/002422.
[86] Johnson et al. (1999) *Bioorg Med Chem Lett* 9:2273-2278.
[87] Evans et al. (2003) *Expert Rev Vaccines* 2:219-229.
[88] Andrianov et al. (1998) *Biomaterials* 19:109-115.
[89] Payne et al. (1998) *Adv Drug Delivery Review* 31:185-196.
[90] U.S. Pat. No. 5,057,540.
[91] WO96/33739.
[92] EP-A-0109942.
[93] WO96/11711.
[94] WO00/07621.
[95] Barr et al. (1998) *Advanced Drug Delivery Reviews* 32:247-271.
[96] Sjolanderet et al. (1998) *Advanced Drug Delivery Reviews* 32:321-338.
[97] Pizza et al. (2000) *Int J Med Microbiol* 290:455-461.
[98] WO95/17211.
[99] WO98/42375.
[100] Singh et all (2001) *J Cont Release* 70:267-276.
[100] WO99/27960.
[101] U.S. Pat. No. 6,090,406
[103] U.S. Pat. No. 5,916,588
[104] EP-A-0626169.
[105] WO99/52549.
[106] WO01/21207.
[107] WO01/21152.
[108] WO02/072012.
[109] Dyakonova et al. (2004) *Int Immunopharmacol* 4(13): 1615-23.
[110] FR-2859633.
[111] Signorelli & Hadden (2003) *Int Immunopharmacol* 3(8):1177-86.
[112] WO2004/064715.
[113] De Libero et al, *Nature Reviews Immunology*, 2005, 5: 485-496
[114] U.S. Pat. No. 5,936,076.
[115] Oki et al, *J. Clin. Investig.*, 113: 1631-1640
[116] US2005/0192248
[117] Yang et al, *Angew. Chem. Int. Ed.*, 2004, 43: 3818-3822
[118] WO2005/102049
[119] Goff et al, *J. Am. Chem., Soc.*, 2004, 126: 13602-13603
[120] WO03/105769
[121] Cooper (1995) *Pharm Biotechnol* 6:559-80.
[122] WO03/011223.
[123] Meraldi et al. (2003) *Vaccine* 21:2485-2491.
[124] Pajak et al. (2003) *Vaccine* 21:836-842.
[125] U.S. Pat. No. 6,586,409.
[126] Wong et al. (2003) *J Clin Pharmacol* 43(7):735-42.
[127] US2005/0215517.
[128] WO90/14837.
[129] Podda & Del Giudice (2003) *Expert Rev Vaccines* 2:197-203.
[130] Podda (2001) *Vaccine* 19: 2673-2680.
[131] *Vaccine Design: The Subunit and Adjuvant Approach* (eds. Powell & Newman) Plenum Press 1995 (ISBN 0-306-44867-X).
[132] *Vaccine Adjuvants: Preparation Methods and Research Protocols* (Volume 42 of *Methods in Molecular Medicine* series). ISBN: 1-59259-083-7. Ed. O'Hagan.
[133] Allison & Byars (1992) *Res Immunol* 143:519-25.
[134] Hariharan et al. (1995) *Cancer Res* 55:3486-9.
[135] US-2007/014805.
[136] WO95/11700.
[137] U.S. Pat. No. 6,080,725.
[138] WO2005/097181.
[139] WO2006/113373.
[140] Han et al. (2005) *Impact of Vitamin E on Immune Function and Infectious Diseases in the Aged at Nutrition, Immune functions and Health* EuroConference, Paris, 9-10 Jun. 2005.
[141] U.S. Pat. No. 6,630,161.
[142] Kandimalla et al. (2003) *Nucleic Acids Research* 31:2393-2400.
[143] WO02/26757.
[144] WO99/62923.
[145] Krieg (2003) *Nature Medicine* 9:831-835.
[146] McCluskie et al. (2002) *FEMS Immunology and Medical Microbiology* 32:179-185.
[147] WO98/40100.
[148] U.S. Pat. No. 6,207,646.
[149] U.S. Pat. No. 6,239,116.
[150] U.S. Pat. No. 6,429,199.
[151] Kandimalla et al. (2003) *Biochemical Society Transactions* 31 (part 3):654-658.
[152] Blackwell et al. (2003) *J Immunol* 170:4061-4068.
[153] Krieg (2002) *Trends Immunol* 23:64-65.
[154] WO01/95935.
[155] Kandimalla et al. (2003) *BBRC* 306:948-953.
[156] Bhagat et al. (2003) *BBRC* 300:853-861.
[157] WO03/035836.
[158] WO01/22972.
[159] Thompson et al. (2005) *J Leukoc Biol* 78: 'The low-toxicity versions of LPS, MPL® adjuvant and RC529, are efficient adjuvants for CD4+ T cells'.
[160] UK patent application GB-A-2220211.
[161] WO 94/21292.
[162] WO94/00153.
[163] WO95/17210.
[164] WO96/26741.
[165] WO93/19780.
[166] Gennaro (2000) *Remington: The Science and Practice of Pharmacy*. 20th edition, ISBN: 0683306472.
[167] Banzhoff (2000) *Immunology Letters* 71:91-96.
[168] Nony et al. (2001) *Vaccine* 27:3645-51.
[169] WO2005/089837.
[170] U.S. Pat. No. 6,692,468.
[171] WO00/07647.
[172] WO99/17820.
[173] U.S. Pat. No. 5,971,953.
[174] U.S. Pat. No. 4,060,082.
[175] EP-A-0520618.
[176] WO98/01174.
[177] Potter & Oxford (1979) *Br Med Bull* 35: 69-75.
[178] Greenbaum et al. (2004) *Vaccine* 22:2566-77.
[179] Zurbriggen et al. (2003) *Expert Rev Vaccines* 2:295-304.
[180] Piascik (2003) *J Am Pharm Assoc* (Wash D C). 43:728-30.
[181] Mann et al. (2004) *Vaccine* 22:2425-9.
[182] Halperin et al. (1979) *Am J Public Health* 69:1247-50.
[183] Herbert et al. (1979) *J Infect Dis* 140:234-8.
[184] Chen et al. (2003) *Vaccine* 21:2830-6.

We claim:

1. A method for immunizing a patient against an influenza virus infection with a two-dose regimen, the method comprising a step of:
  administering to a patient a second dose of an influenza virus vaccine by a second route of administration, wherein the patient has previously received within a single influenza season a first dose of the influenza virus vaccine by a first route of administration; wherein the first dose comprises a first adjuvant; wherein the first route of administration is the same as the second route of administration; further wherein the second dose of the influenza virus vaccine does not comprise the first adjuvant.

2. The method of claim 1, wherein the patient has previously received the first dose at least about 2 weeks, about 3 weeks, about 4 weeks, about 6 weeks, about 8 weeks, about 10 weeks, about 12 weeks, or about 16 weeks prior within the single influenza season.

3. The method of claim 1, wherein the second dose comprises a second adjuvant, and wherein the second adjuvant is different from the first adjuvant.

4. The method of claim 1, wherein the first and second route of administration is by intramuscular injection.

5. The method of claim 1, wherein the first dose is adjuvanted with an oil-in-water emulsion adjuvant.

6. The method of claim 5, wherein the oil-in-water emulsion adjuvant comprises squalene.

7. The method of claim 6, wherein the oil-in-water emulsion adjuvant comprises squalene and one or more surfactants.

8. The method of claim 7, wherein the oil-in-water emulsion adjuvant comprises 0.1-1% surfactants.

9. The method of claim 7, wherein the oil-in-water emulsion adjuvant comprises squalene, polysorbate 80, and sorbitan trioleate.

10. The method of claim 1, wherein the influenza virus vaccine comprises an influenza virus antigen selected from the group consisting of:
  H1, H2, H3, H5, H7 and H9 influenza A virus subtypes.

11. A method for immunizing a patient against at least one influenza virus infection with a two-dose regimen, comprising the steps of:
  (i) administering a first dose of an influenza virus vaccine comprising at least an inactivated influenza antigen in combination with a first adjuvant which comprises an oil-in-water emulsion; and
  (ii) administering a further dose of the influenza virus vaccine, wherein the further dose of the influenza virus vaccine does not comprise the first adjuvant, within six months after administering the dose in step (i).

12. The method of claim 11, wherein the further dose is administered by the same route as the first dose.

13. The method of claim 11, wherein the further dose is adjuvanted with an adjuvant that is different from the first adjuvant.

14. The method of claim 11, wherein the oil-in-water emulsion includes a terpenoid.

15. The method of claim 14, wherein the terpenoid is squalene.

16. The method of claim 11, wherein the oil-in-water emulsion includes polyoxyethylene sorbitan monooleate, sorbitan trioleate, lecithin or octoxynol-9.

17. The method of claim 11, wherein the first and/or further doses of the influenza virus vaccine comprise antigens from 2, 3, or 4 influenza virus strains.

18. The method of claim 11, wherein the further dose of the influenza virus vaccine and the first dose are both administered by intramuscular injection.

19. The method of claim 11, wherein the first and/or further doses of the influenza virus vaccine are administered to a patient less than 1 year old, 1-5 years old or 5-15 years old.

20. The method of claim 11, wherein the first and further doses of the influenza virus vaccine share at least one common hemagglutinin subtype.

21. The method of claim 11, wherein the first and further doses of the influenza virus vaccine comprise antigens from pandemic influenza strains.

22. The method of claim 11, wherein the first and further doses of the influenza virus vaccine comprise an antigen from H5N1, H5N3, H9N2, H2N2, H7N1 or H7N7 influenza.

* * * * *